United States Patent
Aboul-Hosn

[19]

[11] Patent Number: 6,083,260
[45] Date of Patent: *Jul. 4, 2000

[54] REVERSE FLOW TRANSPORT PUMP AND ORGAN STABILIZATION APPARATUS INCLUDING RELATED METHODS

[75] Inventor: Walid Aboul-Hosn, Sacramento, Calif.

[73] Assignee: A-Med Systems, Inc., Sacramento, Calif.

[ * ] Notice: This patent is subject to a terminal disclaimer.

[21] Appl. No.: 08/933,566

[22] Filed: Sep. 19, 1997

Related U.S. Application Data

[63] Continuation-in-part of application No. 08/891,456, Jul. 11, 1997.

[51] Int. Cl.[7] .................................................. A61N 1/03
[52] U.S. Cl. ................................................. 623/3; 600/16
[58] Field of Search .................................. 623/3; 600/17, 600/16; 604/43, 4; 415/900; 417/168, 172

[56] References Cited

U.S. PATENT DOCUMENTS

| | | |
|---|---|---|
| 3,995,617 | 12/1976 | Watkins et al. . |
| 4,116,589 | 9/1978 | Rishton . |
| 4,129,129 | 12/1978 | Amrine . |
| 4,567,882 | 2/1986 | Heller . |
| 4,625,712 | 12/1986 | Wampler . |
| 4,704,121 | 11/1987 | Moise . |
| 4,753,221 | 6/1988 | Kensey et al. ............................ 600/16 |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |
| 4,898,518 | 2/1990 | Hubbard et al. . |
| 4,906,229 | 3/1990 | Wampler . |
| 4,908,012 | 3/1990 | Moise et al. . |
| 4,944,722 | 7/1990 | Carriker et al. . |
| 4,955,856 | 9/1990 | Phillips ....................................... 623/3 |
| 4,969,865 | 11/1990 | Hwang et al. . |
| 4,985,014 | 1/1991 | Orejola . |
| 5,009,636 | 4/1991 | Wortley et al. . |
| 5,049,134 | 9/1991 | Golding et al. .......................... 604/151 |

(List continued on next page.)

FOREIGN PATENT DOCUMENTS

| | | |
|---|---|---|
| 280 225 | 8/1988 | European Pat. Off. . |
| 0 768 091 | 4/1997 | European Pat. Off. . |
| 768 091 | 4/1997 | European Pat. Off. . |
| 2233 293 | 1/1973 | Germany . |
| 286 145 | 1/1971 | U.S.S.R. . |
| 545 358 | 7/1977 | U.S.S.R. . |
| WO 97/40751 | 11/1997 | WIPO . |

*Primary Examiner*—Bruce Snow
*Attorney, Agent, or Firm*—Jonathan Spangler

[57] ABSTRACT

A reverse flow pump for transporting bodily fluids comprising an outer pump housing formed with concentric inner and outer passageways, a rotatedly fixed rotor positioned within the pump housing, and an interior compartment surrounding at least a portion of the rotor in communication with the inner and outer pump housing passageways. A hubless reverse flow rotor is further provided comprising a central portion formed with a passageway for the directional flow of fluid relative to the rotor in a spaced apart relation to a base portion to permit the reverse flow of fluid relative to the rotor. A reverse flow pump and coaxial lumen system if also provided comprising a pair of concentric conduits formed of different lengths for the directionally opposed transport of fluids including blood within a closed environment such as the heart region wherein the proximal ends of the concentric conduits are substantially aligned with the pump housing to provide continuous flow between the conduits and reversal of fluid flow direction. A stabilization system and related methods for the heart and other bodily organs are further provided that may cooperate with other embodiments of the present invention to maintain circulatory functions while immobilizing surgical sites which may comprise a cannula and an inflatable stabilization balloon for internally supporting a heart or organ wall in cooperation with externally applied surgical instruments.

13 Claims, 23 Drawing Sheets

U.S. PATENT DOCUMENTS

| | | | |
|---|---|---|---|
| 5,100,383 | 3/1992 | Lichtenstein | 600/16 |
| 5,112,349 | 5/1992 | Summers et al. | 623/3 |
| 5,167,223 | 12/1992 | Koros et al. . | |
| 5,234,456 | 8/1993 | Silvestrini . | |
| 5,393,207 | 2/1995 | Maher et al. . | |
| 5,456,667 | 10/1995 | Ham et al. . | |
| 5,478,309 | 12/1995 | Sweezer, Jr. et al. . | |
| 5,588,812 | 12/1996 | Taylor et al. . | |
| 5,695,471 | 12/1997 | Wampler . | |
| 5,707,218 | 1/1998 | Maher et al. . | |
| 5,718,678 | 2/1998 | Fleming III | 604/43 |
| 5,727,569 | 3/1998 | Benetti et al. . | |
| 5,755,784 | 5/1998 | Jarvik | 600/16 |
| 5,765,568 | 6/1998 | Sweezer et al. . | |
| 5,782,797 | 7/1998 | Schweich, Jr. et al. . | |
| 5,785,686 | 7/1998 | Runge | 604/96 |
| 5,800,375 | 9/1998 | Sweezer et al. . | |
| 5,810,757 | 9/1998 | Sweezer, Jr. et al. . | |

FIG.—2

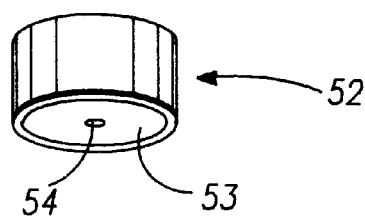
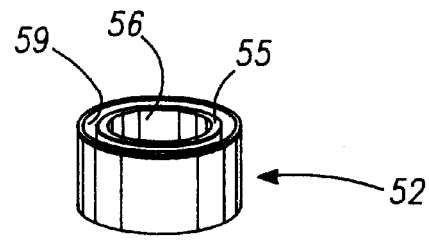
FIG.—5A                FIG.—5B
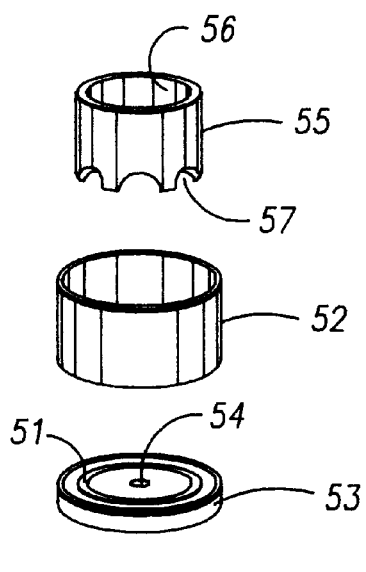
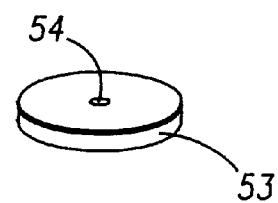
FIG.—5C                FIG.—5D

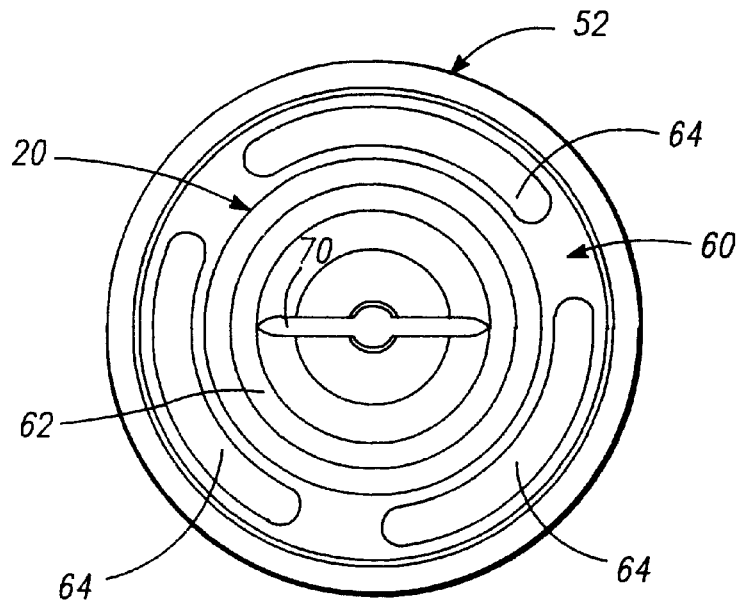
FIG. —6A
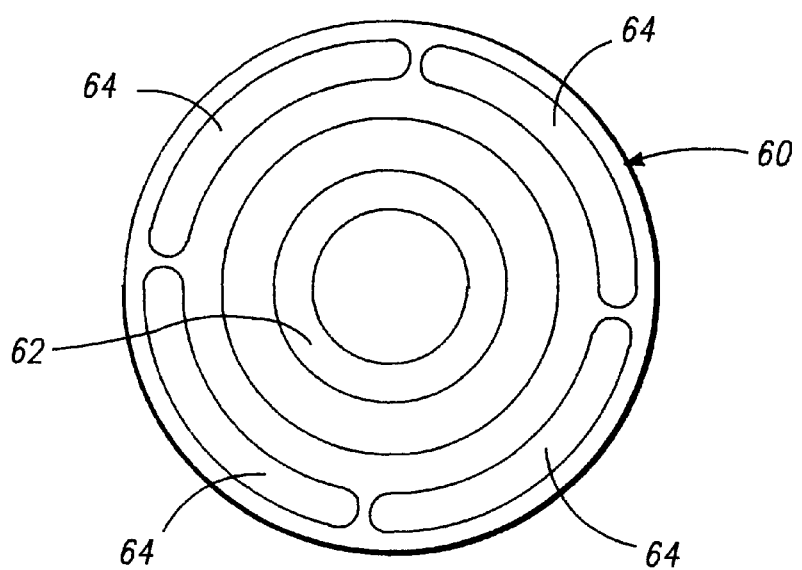
FIG. —6B

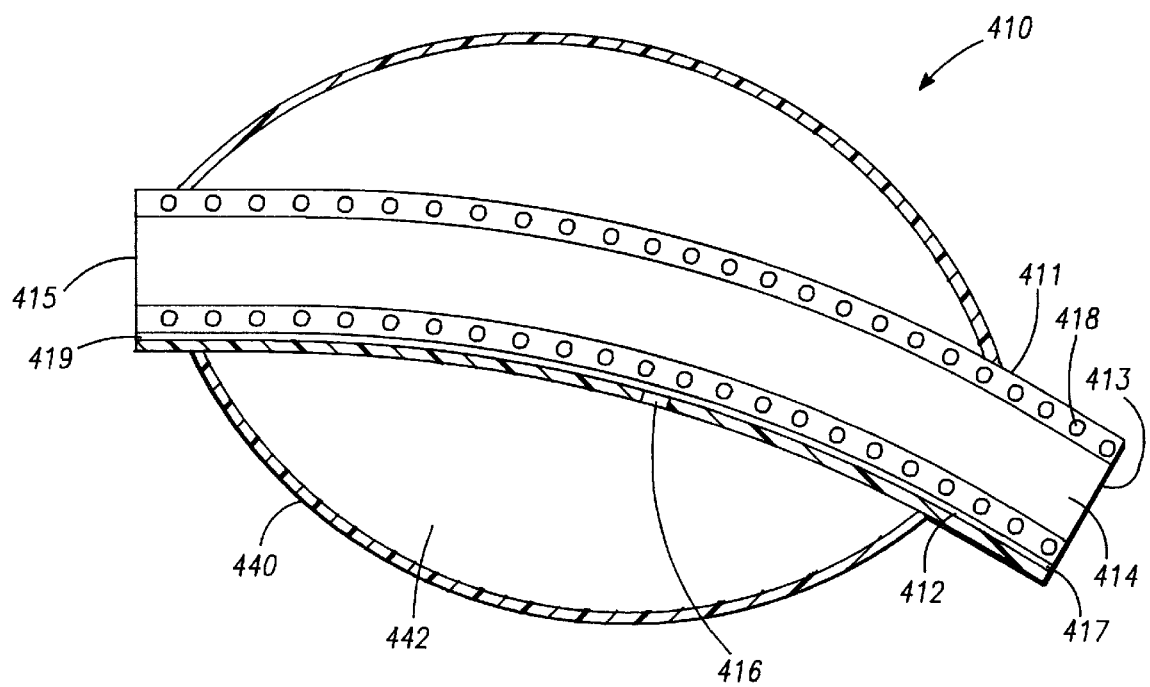
FIG.—20

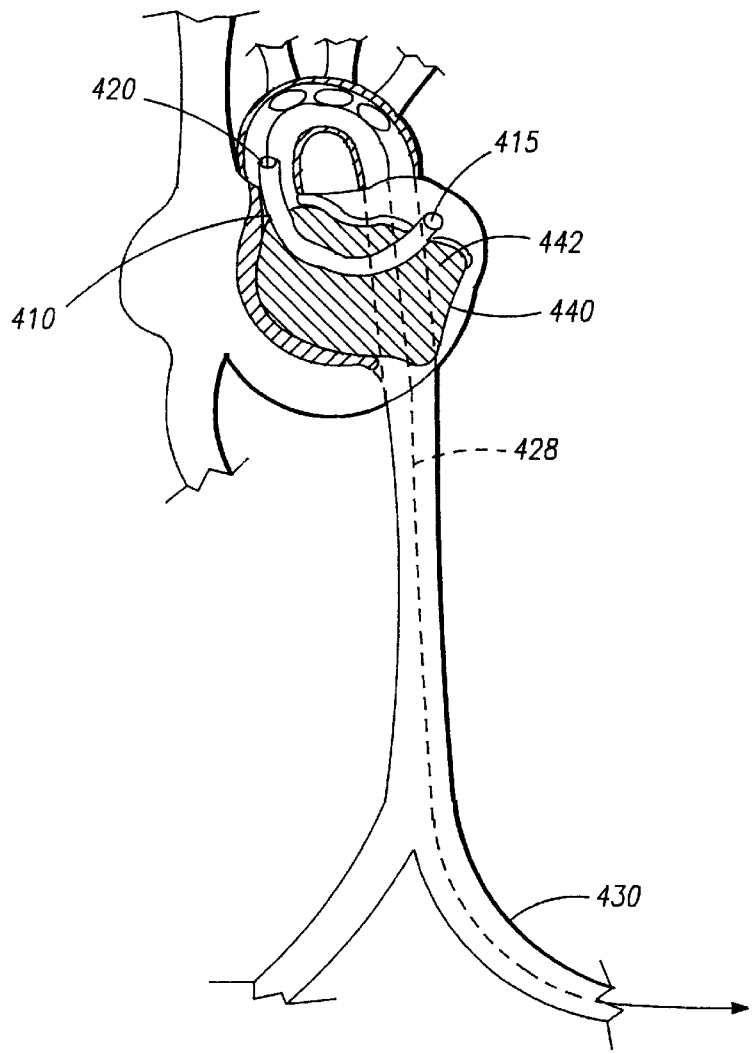
FIG.—21
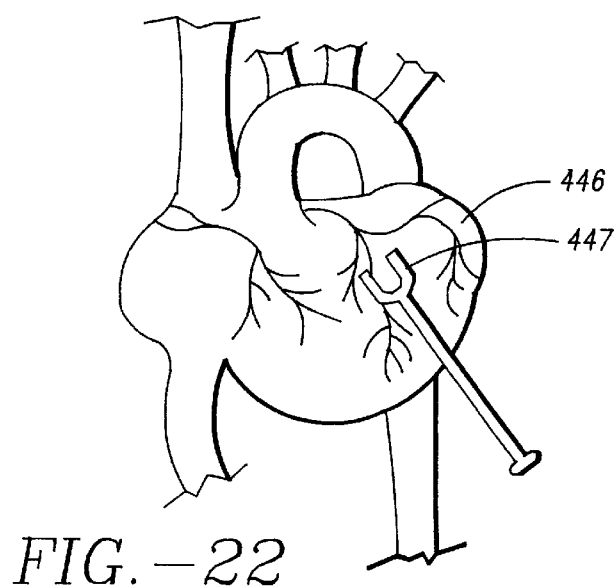
FIG.—22

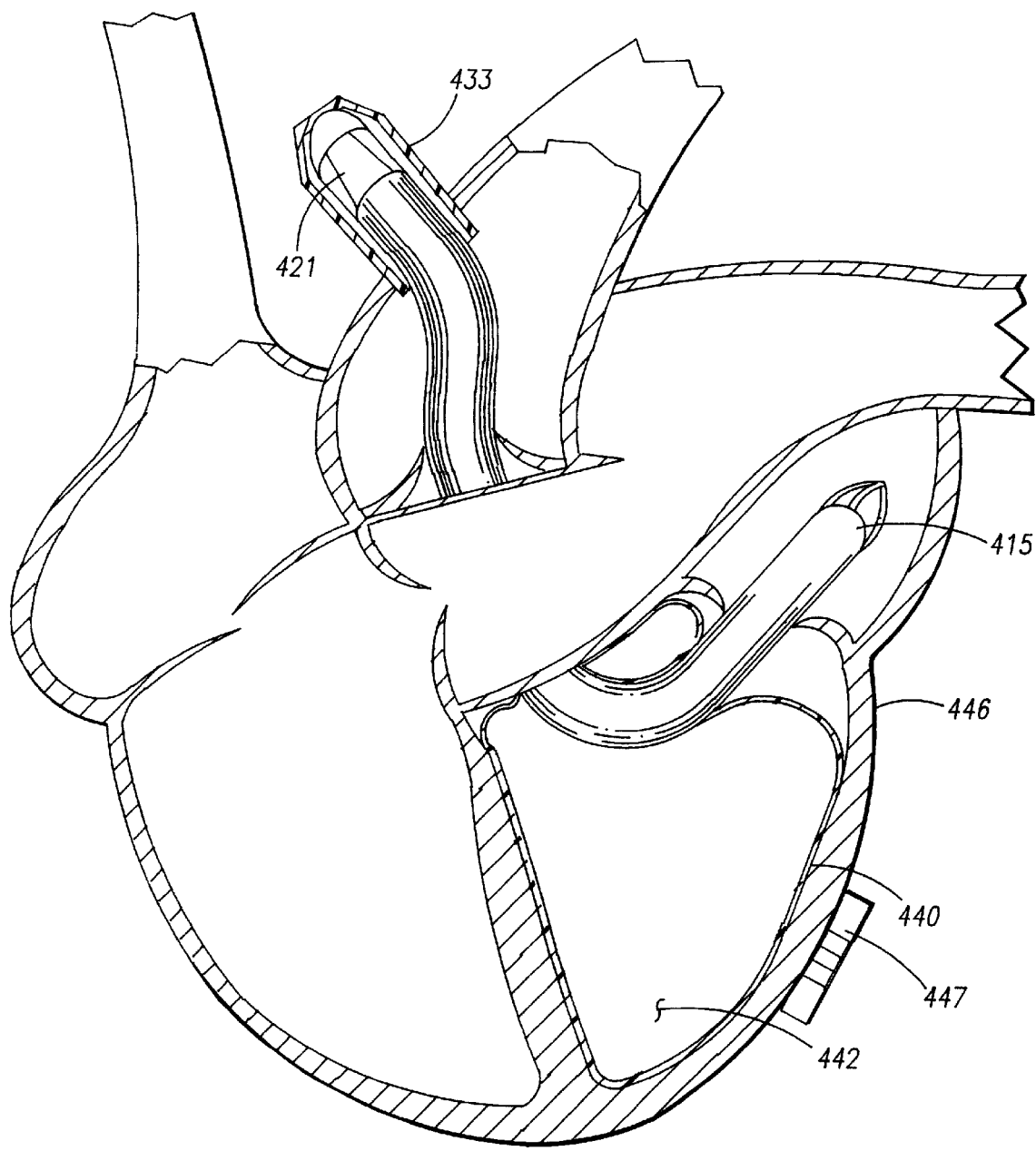
FIG.—24

REVERSE FLOW TRANSPORT PUMP AND ORGAN STABILIZATION APPARATUS INCLUDING RELATED METHODS

This application is a continuation-in-part application of pending U.S. patent application Ser. No. 08/891,456 filed on Jul. 11, 1997.

FIELD OF THE INVENTION

The present invention is generally directed to related apparatus and methods for the circulation of bodily fluids through the use of a reverse flow pump system. More particularly, the present invention relates to the transport of fluids between various body regions and the increased stabilization of body organ.

BACKGROUND OF THE INVENTION

During most surgical procedures, bodily fluids are directed and transferred to various locations with the assistance of artificial pumping apparatus. Major operations such as heart surgery have been accomplished by procedures that require general anesthesia, fall cardiopulmonary bypass (CPB), and complete cessation of cardiopulmonary activity. For example, during open heart surgery, circulation must be maintained while delicate work is performed on fragile blood vessels.

As with most major operations, open heart surgery typically requires weeks of hospitalization and months of recuperation time for the patient. The average mortality rate with this type of procedure is low, but associated with a complication rate that is often much higher. While very effective in many cases, the use of open heart surgery to perform various surgical procedures such as coronary artery bypass grafting (CABG) is highly traumatic to the patient. These procedures require immediate postoperative care in an intensive care unit, a period of hospitalization for at least several days, and an extended recovery period. In addition, open heart procedures require the use of CPB which continues to represent a major assault on a host of body systems. For example, there is noticeable degradation of mental faculties following such surgeries in a significant percentage of CABG patients in the United States. This degradation is commonly attributed to cerebral arterial blockage from debris and emboli generated during the surgical procedure. At the same time, the dramatic increase in the life expectancy of the general population has resulted in patients that are more likely to be older and sicker, with less cardiovascular, systemic, and neurologic reserve. As a consequence, inflammatory, hemostatic, endocrinologic, and neurologic stresses are tolerated much less by a significant number of patients today, and play a more significant role in CPB-induced morbidity.

The CABG procedure generally involves open chest surgical techniques to treat diseased vessels. During this procedure, the sternum of the patient is cut in order to spread the chest apart and provide access to the heart. The heart is stopped, and blood is thereafter cooled while being diverted from the lungs to an artificial oxygenator. In general, a source of arterial blood is then connected to a coronary artery downstream from the occlusion. The source of blood is often an internal artery, and the target coronary artery is typically among the anterior or posterior arteries which may be narrowed or occluded.

The combined statistics of postoperative morbidity and mortality continue to illustrate the shortcomings of CPB. The extracorporeal shunting and artificially induced oxygenation of blood activates a systemwide roster of plasma proteins and blood components in the body including those that were designed to act locally in response to infection or injury. When these potent actors are disseminated throughout the body without normal regulatory controls, the entire body becomes a virtual battleground. The adverse hemostatic consequences of CPB also include prolonged and potentially excessive bleeding. CPB-induced platelet activation, adhesion, and aggregation also contribute to a depletion in platelet number, and is further compounded by the reversibly depressed functioning of platelets remaining in circulation. The coagulation and fibrinolytic systems both contribute to hemostatic disturbances during and following CPB. However, the leading cause of morbidity and disability following cardiac surgery is cerebral complications. Gaseous and solid micro and macro emboli, and less often perioperative cerebral hypoperfusion, produce neurologic effects ranging from subtle neuropsychologic deficits to fatal stroke. Advances in computed tomography, magnetic resonance imaging, ultrasound, and other imaging and diagnostic techniques have added to the understanding of these complications. But with the possible exception of perioperative electroencephalography, these technologies do not yet permit real time surgical adjustments that are capable of stopping a stroke in the making. Doppler and ultrasound evaluation of the carotid artery and ascending aorta, and other diagnostic measures, can also help identify surgical patients at elevated risk for stroke which are among the growing list of pharmacologic and procedural measures for reducing that risk.

CPB also affects various endocrine systems, including the thyroid gland, adrenal medulla and cortex, pituitary gland, pancreas, and parathyroid gland. These systems are markedly affected not only by inflammatory processes, but also by physical and biochemical stresses imposed by extracorporeal perfusion. Most notably, CPB is now clearly understood to induce euthyroid-sick syndrome which is marked by profoundly depressed triiodothyronine levels persisting for days following cardiothoracic surgery. The efficacy of hormone replacement regimens to counteract this effect are currently undergoing clinical investigation. By contrast, levels of the stress hormones epinephrine, norepinephrine, and cortisol are markedly elevated during and following CPB, and hyperglycemia is also possible.

Alternatives to CPB are limited to a few commercially available devices that may further require major surgery for their placement and operation such as a sternotomy or multiple anastomoses to vessels or heart chambers. For example, some present day devices used in CPB may require a sternotomy and an anastomosis to the ascending aorta for placement. The main drawbacks of these devices include their limited circulatory capacity which may not totally support patient demands, and their limited application for only certain regions of the heart such as a left ventricular assist device. These types of devices typically require direct access to heart region and open heart surgery. Other available devices that permit percutaneous access to the heart similarly have disadvantages such as their limited circulatory capabilities due to the strict size constraints for their positioning even within major blood vessels. Moreover, the relative miniaturization of these types of devices present a high likelihood of mechanical failure. In further attempts to reduce the physical dimensions for cardiac circulatory apparatus, or any other bodily fluid transport system, the flow capacity of these devices are significantly diminished.

It would therefore be desirable to provide other less traumatic and more efficacious methods and techniques for controlling fluids while performing heart surgery or any other type of major operation. It would be particularly desirable if such techniques did not require the use of CPB or a sternotomy. It would be even more desirable if such apparatus and techniques could be performed using thoracoscopic methods that have been observed to decrease morbidity and mortality, cost, and recovery time when compared to conventional open surgical procedures.

Another significant disadvantage of surgical procedures on the heart and other fluid transport systems within the body is their inherent structural instability. The relative flexibility and wide range of movement of organ walls, cavities or the like often complicates delicate procedures that demand a stable operating platform. For example, the instability of unsupported cardiac walls, particularly when the heart is still beating, present significant challenges to the surgeon in performing CABG or other similar procedures. A variety of tools or probes are currently used in an attempt to minimize the movement of a tissue wall, organ or cavity wall, such as the exterior heart wall, and is a well recognized method used during CABG surgery on a beating heart. For example, a probe may be used that consists of a forked pedal placed directly onto the surface of a beating heart. These devices and other similar implements simply compress the outside wall of the heart or any other body relatively unstable surface to reduce its movement, and allows a surgeon to operate in a slightly more controlled environment. Other commonly used tools that provide similar functions may consist of a series of suction cups that uses suction force to suspend or hold areas surrounding the external surface of a surgical site in order to reduce undesirable movement. These and other known devices generally hold or immobilize only the external surface of an organ or unsupported wall to reduce movement at the surgical site.

During cardiac surgery, the heart is either still beating or immobilized entirely which requires further use of CPB. In the past, bypass surgery on a beating heart was limited to only a small percentage of patients requiring the surgical bypass of an occluded heart vessel. These patients typically could not be placed on CPB to arrest the heart, and were operated on while the heart kept beating. Meanwhile, patients whose hearts were immobilized and placed on CPB often suffered major side effects as previously described.

The medical community is currently performing more beating heart bypass surgery in an effort to avoid the use of artificial heart-lung machines. The need for apparatus and equipment to minimize the heart movement during surgery is ever increasing but very limited to a small number of devices designed for this specific application. Many devices in use today affect the heart motion by only interacting with its external wall while the inside wall of the heart is free to move about which does not create a motionless surgical site. In bypass surgery, it is particularly desirable to maintain the operating site relatively motionless during the suturing of these small vessels. Any compromise in the quality and integrity of the sutured vessel results in immediate or delayed complication that may be life threatening or require additional surgery. It is therefore desirable to perform beating heart surgery at surgical sites that remain relatively motionless. In order to achieve relative stability with beating heart surgery, it is desirable for the operation site be held relatively motionless by stabilizing both the outside and inside surfaces of the organ, or fixing the external and internal surfaces of a body wall. The stabilization mechanism should also not interfere significantly with the internal flow of fluids such as blood, or interfere with blood circulation by affecting heart rhythm through the application of any significant force to the heart wall, particularly when a patient has a low threshold for manipulating the external wall of the heart. Any significant manipulation of the heart itself may lead to heart fibrillation or arrhythmia, and presents an increased risk to the health of the patient.

SUMMARY OF THE INVENTION

The present invention provides a reverse flow pump system that transports fluid between different regions within the body in order to support a wide variety of surgical procedures. Another object of the present invention is to provide apparatus and methods for the stabilization of surgical sites during procedures such as heart surgery.

In one embodiment of the invention, a reverse flow pump for transporting bodily fluids is provided with concentric inner and outer passageways, and an interior compartment that includes a rotor to reverse the directional flow of fluid relative to the pump. A hubless rotor is also provided for efficiently directing the flow of fluid within conduits adjoining the inner and outer passageways of the pump.

Another embodiment of the present invention provides a thoracoscopic method for cardiac support during surgical procedures. More particularly, the thoracoscopic methods described herein are directed to unloading the heart, and partially or totally stopping the heart to allow procedures to be performed externally on or internally within the heart while the chest may remain unopened. The heart may also be unloaded by using a left ventricular blood pump, or a left and a right ventricular blood pump for venous and arterial circulation.

Another variation of the present invention is directed to an endovascular method and system for preparing the heart for surgical procedures, and particularly for unloading the heart, partially or totally stopping the heart. A reverse flow blood pump system may be passed through a conduit and positioned in a heart chamber or a vessel in preparation to completely or partially stop the heart in order to operate on the organ. Another object of the present invention is to provide a single conduit for introducing a pump system at operative sites in the body with the conduit inserted in the body through a portal of minimal size formed in tissue of a body wall, and engaging an external surface of a vessel or the heart to limit any significant bleeding. An inflow cannula may further be disposed in a heart chamber to direct blood from the heart into a region surrounding the conduit. A single anastomosis may be used to provide a path for both the inflow and the outflow of a blood pump.

An additional object of the present invention is to provide an apparatus which provides cardiac support during open chest heart surgery, or any other surgical procedure that requires total or partial unloading of the patient's heart or complete or partial cessation of heart function, and is less traumatic and invasive to the patient than current apparatus used today.

In yet another embodiment of the present invention, a method and associated apparatus for cardiac support is directed to extravascular or transvalvular procedures that may require only one incision into a major blood vessel such as an aorta. The apparatus may include an elongated inner cannula inserted through a portal formed in a major blood vessel or heart chamber that is disposed coaxially with an outer conduit. A reverse flow pump may be disposed between the proximal openings on the inner cannula and the outer conduit which pumps blood delivered by the inner cannula to the outer conduit. The distal openings on the inner cannula and outer conduit may be spaced apart and disposed either in different blood vessels or transvalvularly in the heart so that blood flowing into the distal opening of the inner cannula may be delivered through the distal opening on the outer conduit located downstream or proximal from the distal opening of the inner cannula. A portal may also be formed in the aorta with the distal opening on the outer conduit extended therethrough. The inner cannula may further be positioned through the aortic valve and disposed inside the left ventricle to transport blood deposited in the aorta thereby unloading the left ventricle. Optional balloons may also be selectively inflated on the outside surface of the inner cannula or outer conduit which act to seal off the passageway between the sides of the blood vessel and the cannula, to cool adjacent tissue, or to deliver drugs to adjacent tissue.

It is another object of this invention to provide stabilization of the external and internal surfaces of the heart wall during cardiac surgery while maintaining normal cardiac and circulatory functions. Another object of the present invention to substantially immobilize the external and internal walls of the heart using an inflatable stabilization balloon or a mechanical structure that supports the inner wall of the heart to provide additional stabilization of a surgical site, and using a forked tool to hold the external surface of the heart to provide stabilization of the outer wall of the heart. Another object of the present invention is to provide a stabilization balloon or a mechanical structure in combination with a flow cannula and pump to allow for normal blood circulation to assist in heart functions. A catheter may further be included comprising an elongated flexible shaft portion with a miniature blood pump and stabilization apparatus positioned at its distal end portion. The catheter may further include a multilumen arrangement to provide separate paths for inflation of a stabilization balloon, a pump drive mechanism, and monitoring or diagnostic apparatus. These and other objects and advantages of the present invention will become more apparent from the following description and accompanying drawings.

BRIEF DESCRIPTION OF THE DRAWINGS

FIGS. 5A–5D are exploded perspective views of the housing and the inlet compartment for a reverse flow pump.

FIGS. 6A and 6B are distal side views of the reverse flow pump unit.

FIG. 20 is a sectional side view of a stabilization balloon with an inflation conduit.

FIG. 21 is a stabilization system provided in accordance with the present invention that is introduced through a femoral artery.

FIG. 22 is an illustration of the exterior view of the heart and a forked instrument used to stabilize an external area of the heart.

FIG. 24 is a partial sectional view of the heart and a stabilization system used in cooperation with extracorporeal pump.

DETAILED DESCRIPTION OF THE INVENTION

Figure 1:
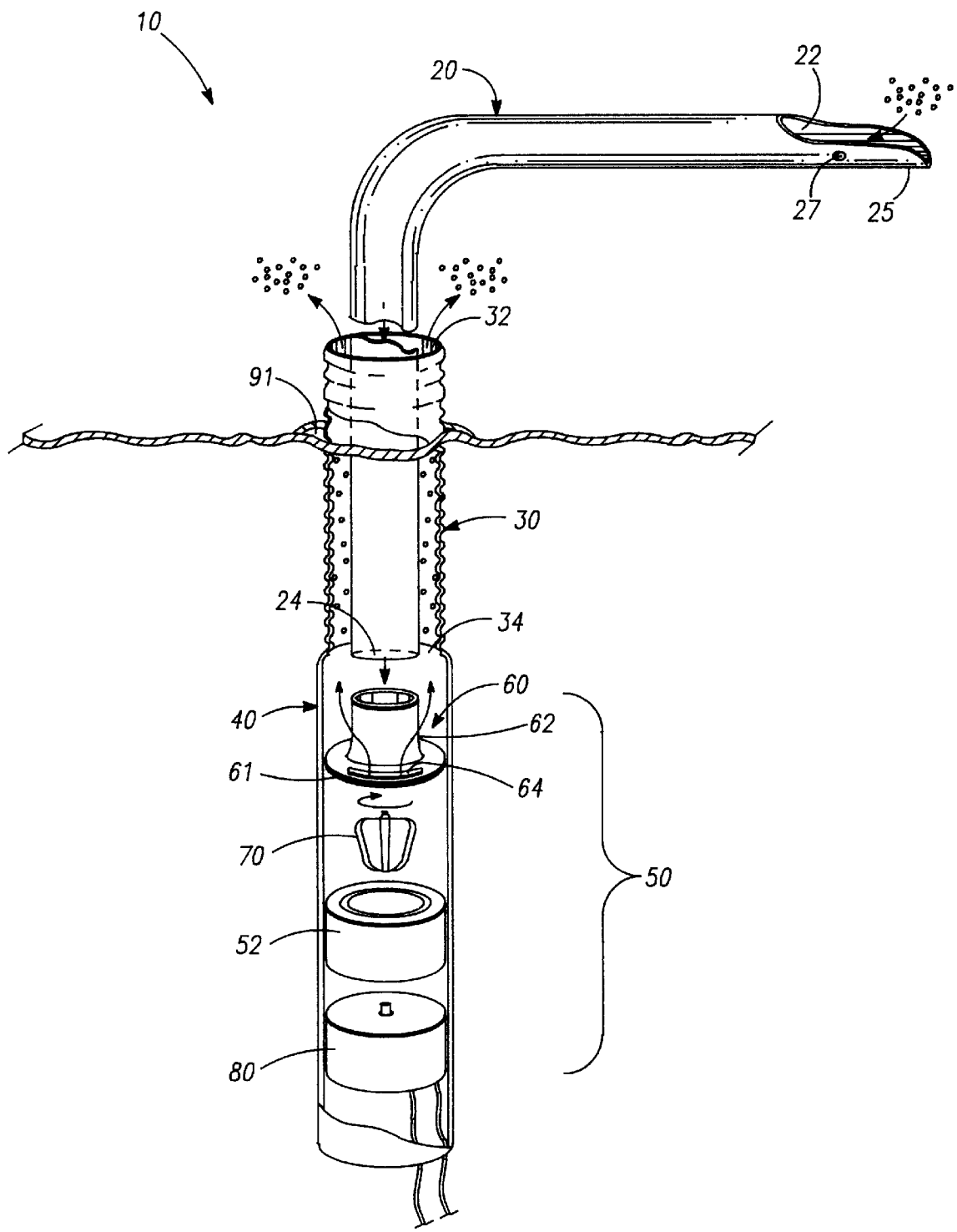
FIG. 1 is an exploded perspective sectional view of a reverse flow system generally showing the reverse flow pump in relation to an inner and an outer conduit which direct and control the flow of fluids between different body regions.

In FIG. 1, a fluid transport system is provided in accordance with one aspect of the present invention. The fluid transport system 10 may comprise an inner cannula 20 coaxially aligned with an outer conduit 30, and a reverse flow pump 50. The reverse flow pump 50 may direct bodily fluids such as blood through the inner cannula 20 to the outer conduit 30, and then throughout other regions of the body. By using such an arrangement, only one portal 91 may be required to be formed in a blood vessel to support various surgical procedures. The inner cannula 20 may be arranged to function as an inlet conduit designed to assist the delivery of blood and other bodily fluids to the pump 50 while the outer conduit 30 may transport fluid away from the pump 50.

It should be understood, however, that the relative functions of the inner cannula and outlet conduit may be exchanged depending on the desired positions of the distal opening 22 of the inner cannula 20 and the distal opening 32 of the outer conduit 30, and the direction of flow controlled by the pump 50.

The inner cannula 20 in FIG. 1 may be formed with a distal opening 22 and a proximal opening 24. When positioned for use during heart surgery, for example, the distal opening 22 may be disposed in a heart chamber through major blood vessels such as the left ventricle. As a result, blood entering the distal opening 22 of the inner cannula 20 is transported to the pump 50 which then directs the blood through the outer conduit 30 to another blood vessel or region of the heart. As with many commercially available cannulas, the inner cannula 20 may be tubular and preferably made of flexible, biocompatible material such as silicone, and may be reinforced with other material such as steel wire to provide sufficient radial stiffness to resist collapsing. The tip 25 of the inner cannula 20 may be chamfered and relatively flexible, or not reinforced, in order to provide greater flexibility and improved advancement of the inner cannula 20 through relatively small vessels or chambers that reduces trauma to surrounding tissue. The inner cannula 20 may also have a plurality of openings 27 formed near its tip 25 to allow blood to flow into the inner cannula 20, particularly when the distal opening 22 may become occluded or otherwise obstructed. A catheter guide wire may also be extended through the cannula openings 27 to dispose the inner cannula 20 at desired locations throughout the body including the heart region. The inner cannula 20 may be formed relatively straight or with a permanent bend having a 10 to 120 degrees curved portion to facilitate installation and removal from a blood vessel or chamber. The inner cannula 20 may also be formed of radiopaque material added or printed on its surface for visibility when exposed to X-ray radiation.

As shown in FIG. 1, the outer conduit 30 of the fluid transport system may be formed with a distal opening 32 and a proximal opening 34. The outer conduit may also be tubular and made of flexible, biocompatible material such as silicone, and may be reinforced with other material such as steel wire to provide sufficient radial stiffness to resist collapsing. The distal opening 32 of the outer conduit 30 may be extended through a portal 91 to form a closed circuit between the inner cannula 20 and outer conduit 30. In a preferred embodiment, the outer conduit 30 is an introducer, or a vascular graft, such as a Dacron™ graft, or any other commercially available grafts or synthetic conduits used. The proximal end of the outer conduit 30 may be further connected to an elongated cylindrical body 40 for positioning and housing of other pump components.

The device represented in FIG. 1 may further comprise an inflow cannula 20 attached to a housing cap 60 fitted over a housing body 52, which houses a rotor 70 coupled to a drive unit 80. The housing cap 60 may further comprise a base member 61 and an inlet neck 62 which may be separate components joined by welding or similar techniques, or may form a unitary body. The base member 61 and the inlet neck 62 are preferably concentric to each other. Outflow windows 64 may also be positioned relatively outwardly to inlet neck 62, and are preferably circumferential and symmetrical to inlet neck 62. The outside diameter of the housing cap 60 is preferably matched to the inside diameter of the housing body 52 for a close tolerance fit, or any other method for attaching the housing cap 60 to the housing body 52. The housing body 52 and the housing cap 60 may also form a unitary body. The outside diameter of the pump 50 may match the inside diameter of a graft 30 so that a hemostatic seal is maintained between the outside diameter of the housing body 52 and the inside diameter of the graft 30. It should be noted again that the present invention may transport and control blood or any other bodily fluid.

Figure 2:
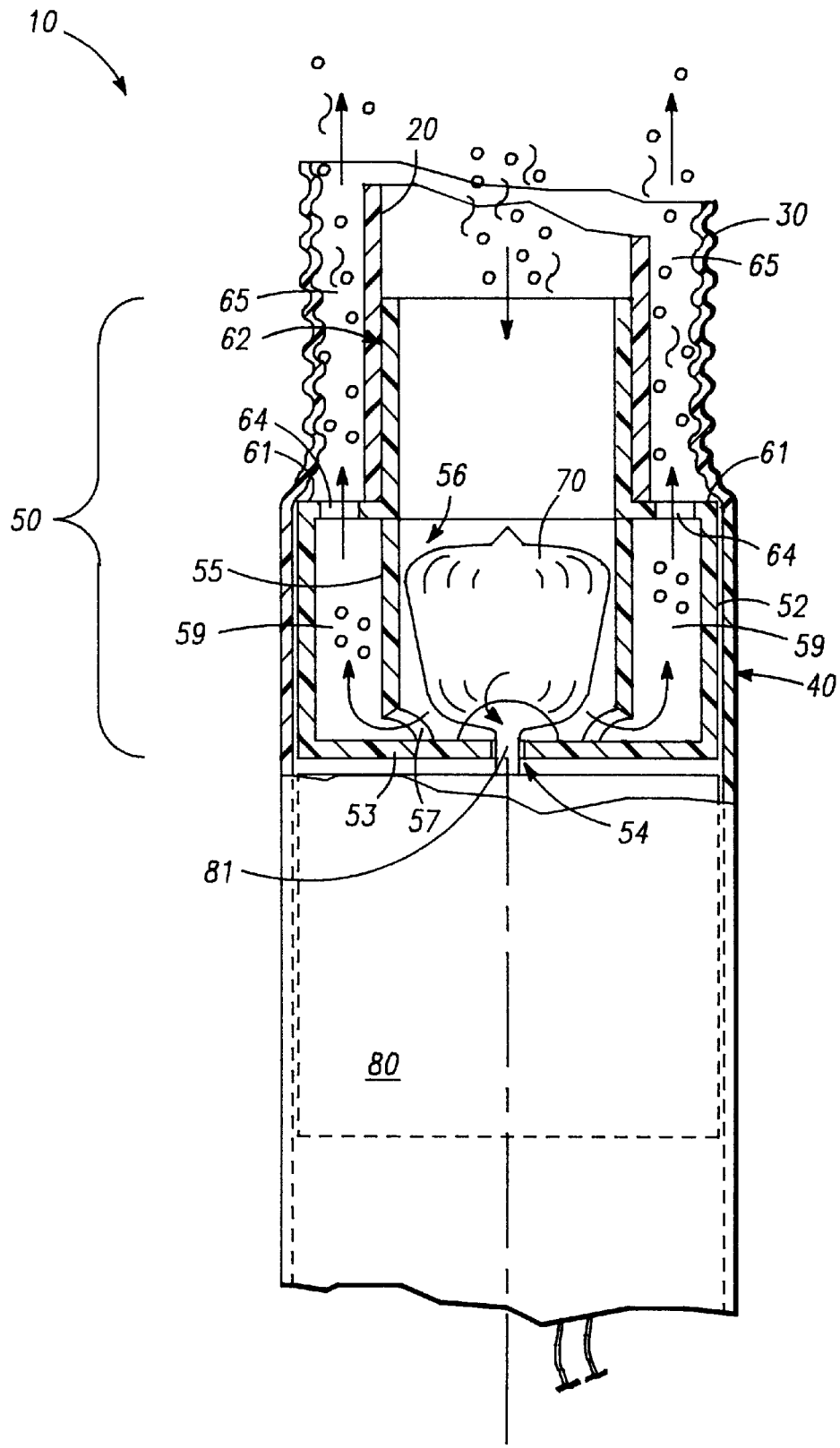
FIG. 2 is a sectional side view of the pump portion of a reverse flow system illustrating the directional change in fluid flow.

As shown in FIG. 2, the pump assembly of the fluid transport apparatus includes a reverse flow pump 50 with coaxially aligned or concentric inlet and outlet ports. The reverse flow pump 50 for this particular embodiment of the present invention further includes a rotor 70 axially aligned inside a cylindrical-shaped housing body 52. The rotor 70 is connected to a drive shaft 81 which is rotated at variable rates of relatively high speed by the driving unit 80. The distal opening of the housing body 52 of the pump 50 may be covered with a housing cap 60. The housing cap 60 is preferably constructed of stainless steel or rigid polymer and may be formed with a plurality of outflow windows 64. The outflow windows 64 may be radially aligned around an inlet neck 62 formed in the base member 61 of the housing cap 60. The housing body 52 illustrated in this embodiment of the present invention is generally cylindrical-shaped and includes a longitudinally and concentrically aligned inlet tube 55. The inlet tube 55 may be integrally attached at one end to the base plate 53 and include a centrally aligned distal opening 56. A plurality of radially aligned cut-outs 57 may also be formed along various portions of the inlet tube 55 to permit the passage of fluid.

A rotor 70 may be disposed longitudinally inside the inlet tube 55 as shown in FIG. 2. During operation of the fluid control apparatus in this configuration, the rotor 70 is rotated by the driving unit 80 through an opening or hole 54 in order to direct fluids such as blood from the inlet tube 55 out through the cut outs 57. The outside diameter of the inlet tube 55 is preferably smaller than the inside diameter of the housing body 52 which creates a passageway 59 between the inlet tube 55 and the housing body 52. A housing cap 60 is attached to the distal opening of the housing body 52. The housing cap 60 may include a circular or disc shaped base member 61 designed to fit over the housing body 52. A cylindrical inlet neck 62 may also be formed perpendicular to and centrally aligned to the base member 61. The outside diameter of the inlet neck 62 is smaller then the inside diameter of both inner cannula 20 and the outer conduit 30 which forms another passageway 65 for the reverse flow of fluid such as blood. The inlet neck 62 may also be joined temporarily or permanently to the proximal opening 24 of the inner cannula 20 by bonding or welding, or may even be integrally formed. The passageway 59 and the outflow windows 64 of the housing cap 60 may be aligned with passageway 65 when the housing cap is assembled with the housing body 52.

The fluid transport apparatus 10 shown in FIGS. 1 and 2 may further include an elongated cylindrical body 40 connected to the proximal opening 34 of the outer conduit 30. The elongated body 40 may house both the pump 50 and the drive unit 80. The cylindrical body 40 may be formed with various dimensions to conveniently provide further assistance in positioning the apparatus 10 in a desired location. The distal opening 22 of the inner cannula 20 and the distal opening 32 of the outer conduit 30 may be spaced apart and located in different blood vessels, for example, or on opposite sides of a heart valve so that blood may be pumped from one blood vessel or chamber to other regions of the heart. The inner cannula 20 and the outer conduit 30 may be coaxially aligned and formed with a sufficient length so that only one portal opening may be required into a major blood vessel, chamber, or any other body passageway. The lengths of the inner cannula 20 and outer conduit 30 may further be varied in accordance with particular applications such as open heart surgery, or during closed heart or other laproscopic procedures which involve forming other openings to provide percutaneous access to inner body regions.

Figure 3:
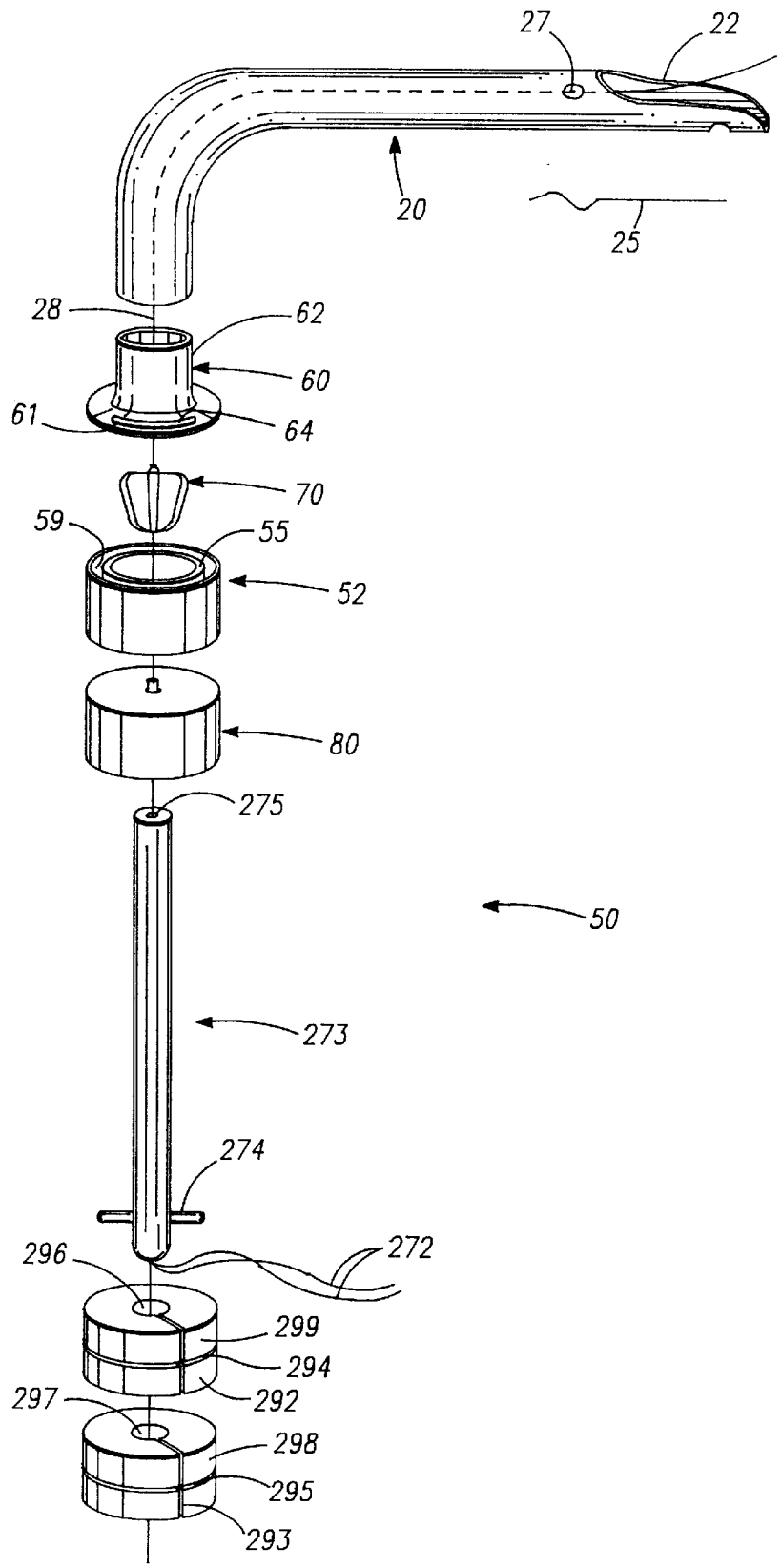
FIG. 3 is an exploded perspective view of a reverse flow pump assembly including a pump driving system and positioning apparatus.
Figure 4:
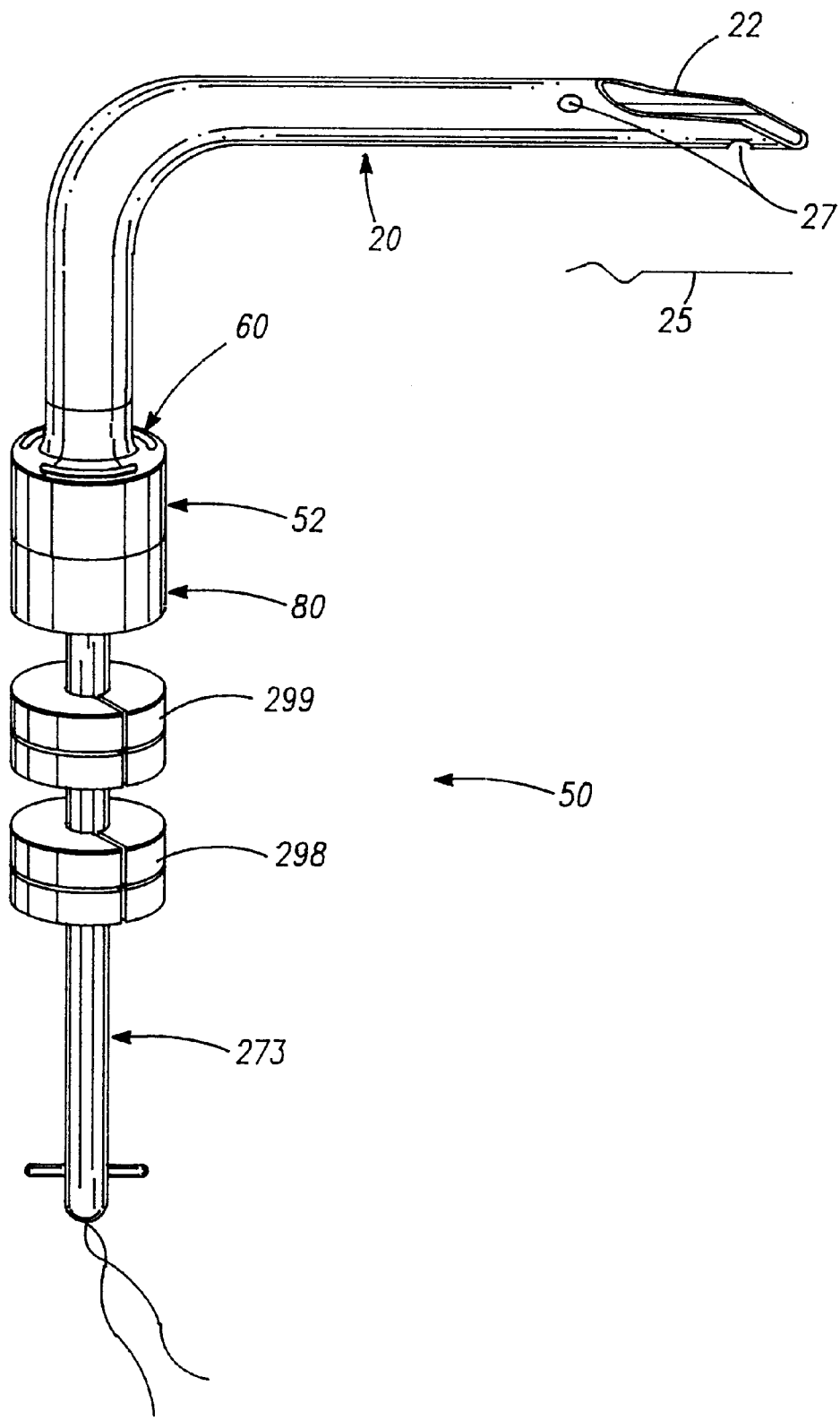
FIG. 4 is a perspective view of an assembled reverse flow pump similarly shown in FIG. 3.

As shown in the perspective views of the reverse flow pump in FIGS. 3 and 4, a positioning rod 273 may be used to allow the transmission of torque or other force from positioning rod proximal end to the drive unit 80 (see FIG. 10) without any significant dampening. The positioning rod 273 is preferably made from a metal or relatively stiff polymer and may comprise a central passage 275 extending the entire length of the positioning rod 273 and used for passing a guiding element 28, such as a guide wire or a catheter or like devices, through its center. The central passage 275 of the positioning rod 273 may form a continuation of a central passage formed in the shaft of drive unit 80, and may be used for passing electrical wire 272 or like elements to the drive unit. The central passage 275 of the positioning rod 273 is also preferably concentric with the outside diameter of positioning rod 273. The distal portion of the positioning rod 273 may be matched to a groove 205 formed in the drive unit 80 to form a press fit, or to attach to the drive unit by welding, bonding or forming a unitary part. The proximal end of the positioning rod 273 may further comprise two handles 274 to assist in the handling of the positioning rod during placement of the pump 50, and to prevent pushing the positioning rod 273 past the handles into a conduit. Since another variation of the present invention provides for the insertion of a left heart pump into a patient's cavity, vessel, or tissue without the use of a guide element 28, the central passage 275 of the positioning rod 273 may therefore be removed or may simply provide for passing wires, tubes or similar accessories needed by the drive unit 80. When a heart pump is inserted unassisted, the inner cannula 20 may simply be advanced by itself into a vessel or chamber.

FIGS. 3 and 4 further illustrate silicone plugs 298 and 299 that may also be used to assist in sealing the pump, and may be formed with resilient flexible material such as silicone or like material. The outside diameter may be matched to the inside diameter of an outer conduit. Central holes 296 and 297 of the distal silicone plugs 298 and 299 are relatively concentric to their outer diameter. Grooves 294 and 295 may be formed circumferentially and midway between the proximal and distal face of the silicone plugs. Slits 292 and 293 may extend through the entire length of the silicone plugs and extend from the outside surface of the silicone plugs to the central holes 296 and 297.

As shown in FIGS. 5A–D, the housing body 52 is preferably tubular and includes a concentric inlet tube 55. When the housing body 52 and the inlet tube 55 are concentric and joined to a base plate 53, a passage 59 is thereby formed for blood or other fluid to flow within. The passage 59 of the housing body 52 and the outflow windows 64 of the housing cap 60 may be aligned when the housing cap and the housing body are assembled coaxially. The inlet tube 55 may comprise multiple cut-outs 57 at its proximal end to connect the passage 59 with the inlet tube 55. The profile of the inlet tube 55 is not necessarily cylindrical and may vary in shape to match the outside profile of the rotor 70. Both profiles may be matched and varied according to pump design, i.e. an axial pump may have a cylindrical profile or a centrifugal pump may have a overall conical profile. A clearance between the inlet tube 55 profile and the rotor 70 should exist to permit the rotor 70 to rotate without contacting the walls of the inlet tube 55. The inlet tube cut-outs 57 may be generally circular, and may depend on the rotor and pump category or application. The proximal end of the inlet tube 55 may be pressed into a matching groove 51 of the base plate 53. The base plate 53 may comprise a groove 51 that is preferably concentric with the base plate 53 circumference, and a central hole 54 that is preferably concentric with the groove 51. The outside diameter of the base plate 53 may be matched to the inside diameter of the housing body 52 to provide an interference fit to hold the base plate 53 and the housing body 52 together. The base plate 53 and the housing body 52 may be formed of a unitary part or a multiple parts joined together by known techniques such as welding, bonding, or like techniques. The housing body 52 proximal end may be attached to the distal end of drive unit 80.

FIGS. 6A and 6B are distal side views of the reverse flow pump unit. In FIG. 6A, the housing cap 60 is illustrated as having an inlet neck 62 and outflow windows 64. The inner cannula 20 circumferentially surrounds the inlet neck 62 to direct fluid towards pump unit. The shape and relative number of windows 64 in the housing cap 60 may of course vary. Although shown as a substantially concentric circular configuration, the particular shape of the housing cap 60 and inlet neck 62 may also vary. The rotor 70 within the housing body 52 may be configured and rotate in a direction that would permit fluid to enter the pump through the housing windows 64 and directed away from the pump through the neck 62 of the housing cap. FIG. 6B illustrates yet another variation of the housing cap 60 for the pump unit, and may be selected to cooperate in particular with the operation of a hubless rotor (shown in FIG. 8) for the reverse flow pump. Although the housing cap windows 64 are shown to be circumferentially surrounded by a centrally located housing cap neck opening 62, the spacing, position and geometry of these passageways may be varied. The housing cap neck opening 62 may also vary in size and accommodate various inner cannula diameters.

Figure 7A:
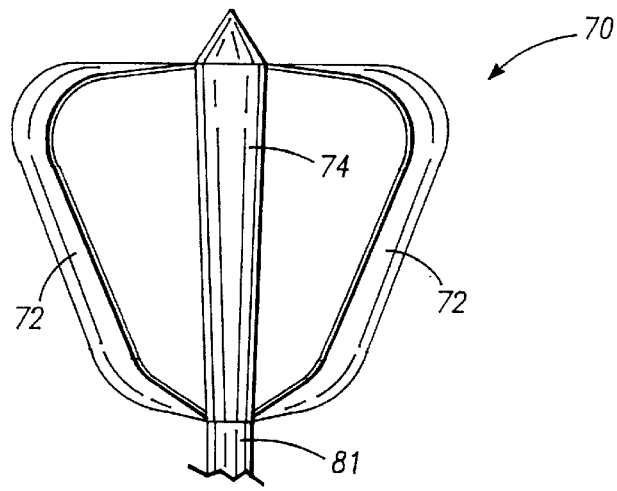
FIGS. 7A–7C are side and sectional views of a rotor for a reverse flow pump having a hub and blade portions.
Figure 7B:
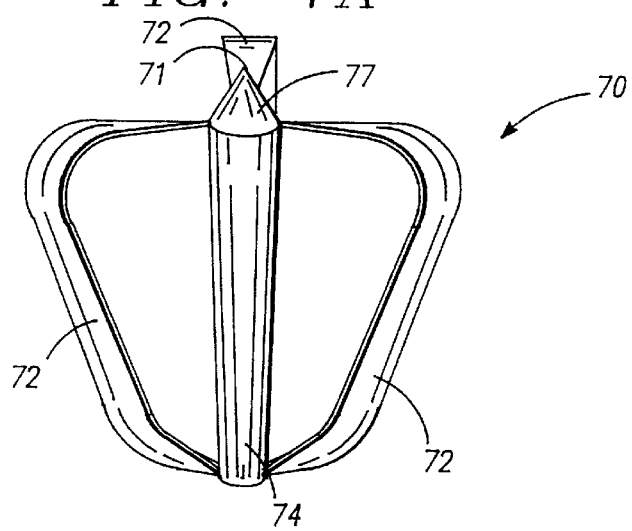
Figure 7C:
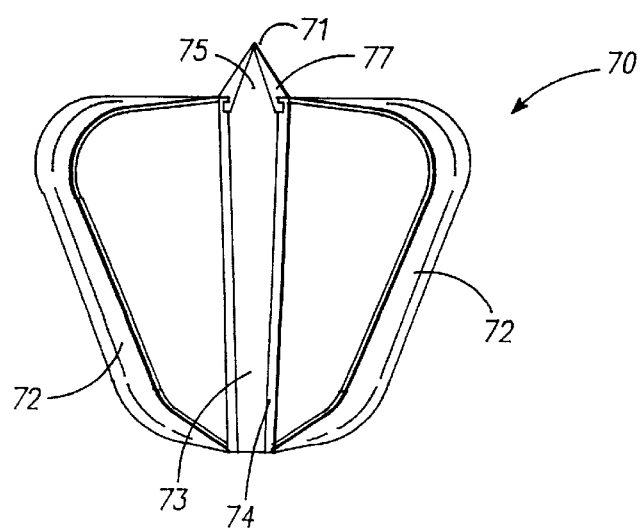

FIGS. 7A–C and 8 illustrate various configurations of a rotor 70 that may be used in a reverse flow pump or any other type of fluid transport apparatus. As shown in FIGS. 7A–C, the rotor 70 may comprise a single or multiple blades 72 extending from a longitudinally aligned central hub 74. The blades 72 of the rotor 70 assist in directing and controlling fluid direction. Accordingly, the reverse flow pump may generate flow rates of up to 8 or 9 liters per minute depending upon the particular pump dimensions and configuration, and is fully capable of supporting circulatory functions of the heart.

The rotor 70 is preferably an axial or a centrifugal hydraulic rotor, and profiled to provide lift to surrounding fluid when the rotor is rotated. As shown in FIG. 7C, a central rotor passage 73 may extend the entire length of the rotor 70 and preferably forms a continuation of central passage 82 of drive unit 80. The central rotor passage 73 of the rotor 70 may be left open or closed at the distal end of passage 73 with a gland valve 77 or similar closure entities to help keep blood or fluid outside of the passage. The disclosed gland valve 77 is presented as an example and is not meant to be the only method that may be used in keeping the fluid outside of passage 73 of the rotor 70. Gland valve 77 may be made from a flexible and resilient material such as silicone. The gland valve 77 may further comprise a central conical opening 75 with a diameter of 0.040 inches at the proximal end of the valve gland and a slit 71 at the distal end of the gland valve. The slit 71 may allow the passage of commercially available guide wires or similar devices for guiding the pump to its intended placement, and may also close and provide sufficient hemostasis when the guide wire or similar devices are removed from the gland valve 77. When no guide wire is used to position the pump assembly, the central rotor passage 73 of the rotor 70 may be removed entirely, and the gland valve 77 may be replaced with a conical or bullet shaped metallic or polymeric cap that is similar to the outside profile of the gland valve and formed without a slit 71.

Figure 8:
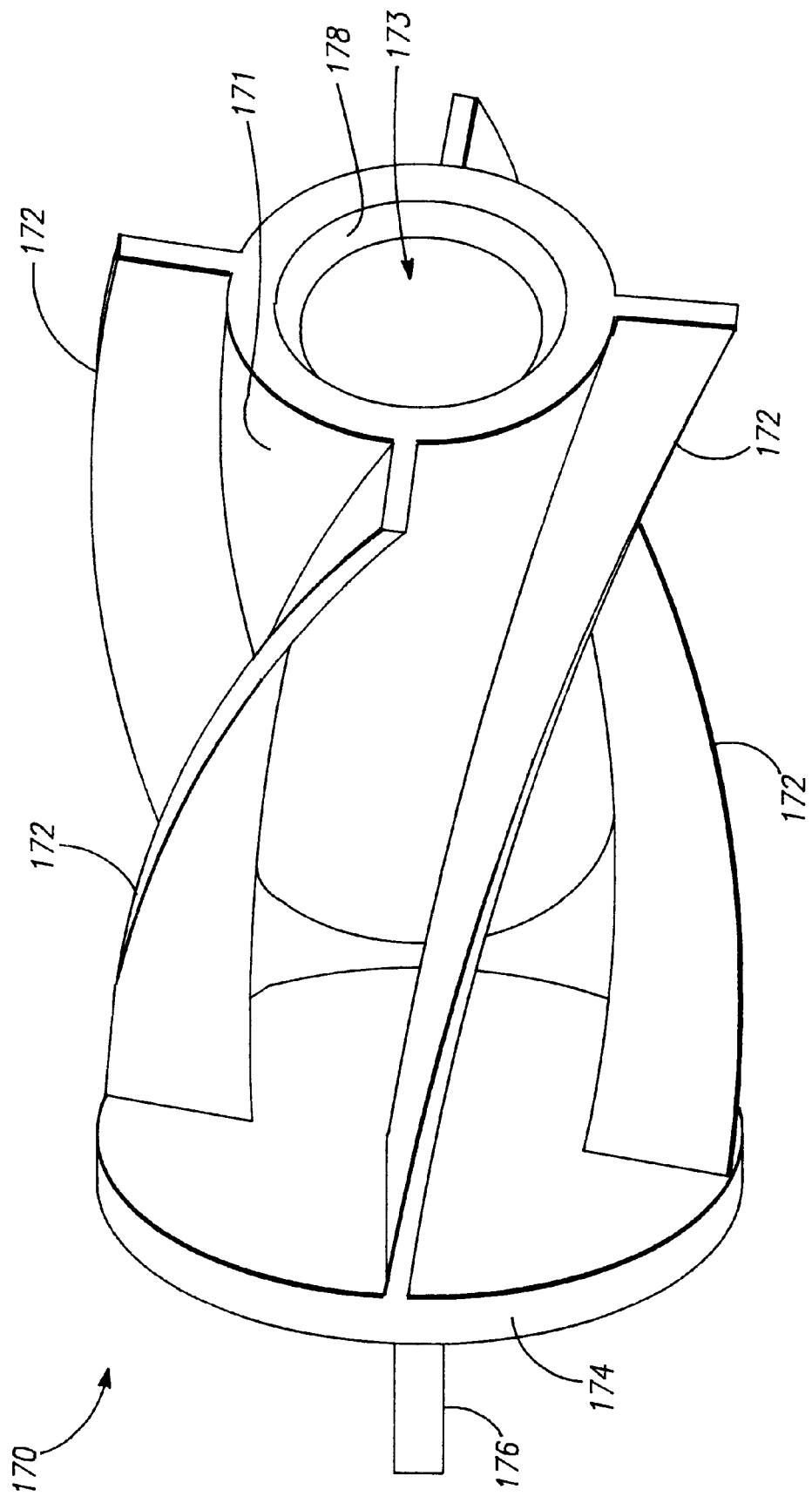
FIG. 8 is a perspective view of a hubless rotor for a reverse flow pump having a central passageway and blade portions.

In accordance with another variation of the present invention, as shown in FIG. 8, a hubless rotor 170 may be selected for the reverse flow pump system. The hubless rotor 170 may include a central portion 171 with an open central passageway 173 to permit the directional flow of fluid relative to the pump and an external surface with rotor blades 172 to reverse and direct the flow of fluid away from the pump. A base portion 174 and the rotor blades 172 may be selected to position and support the center portion 171 of the hubless rotor 170. The base portion 174 may be disc shaped and may include a shaft 176 that is directly or indirectly connected to a rotor drive unit. Although the blades 172 of the illustrated embodiment also support the center portion 171, it is understood that the supporting members may also be separately formed from the blades. The central portion 171 of the hubless rotor may be generally formed with a cylindrical geometry or other suitable configurations to permit the directional flow of fluid through the center region of the hubless rotor 170 and the reverse flow of fluid along the relatively outer region of the rotor. The particular rotor blades 172 shown in FIG. 8 are generally formed in spiral or helical pattern, but may similarly have other configurations to effectively direct fluid to enter and exit the pump.

Figure 9A:
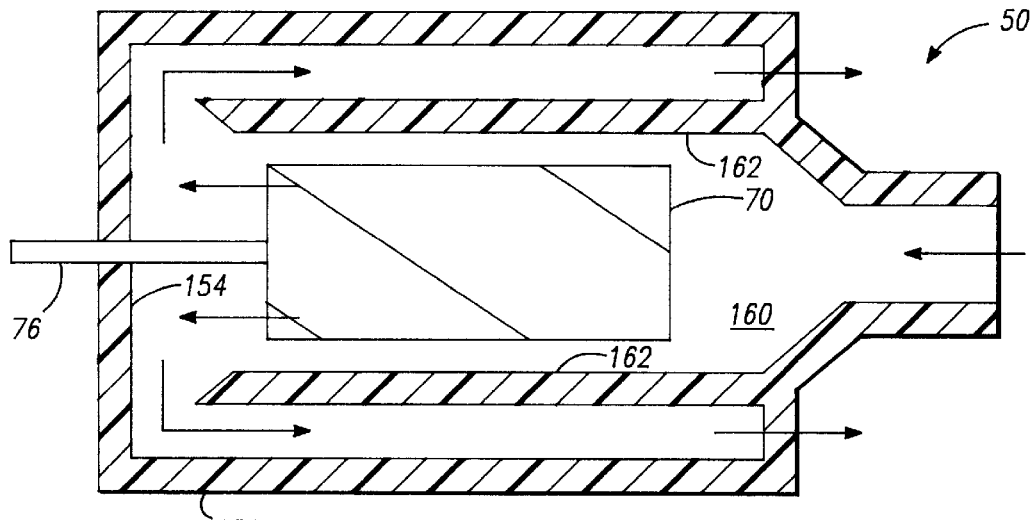
FIGS. 9A–E are sectional views of various pump housings with their respective rotors and relative flow patterns.
Figure 9B:
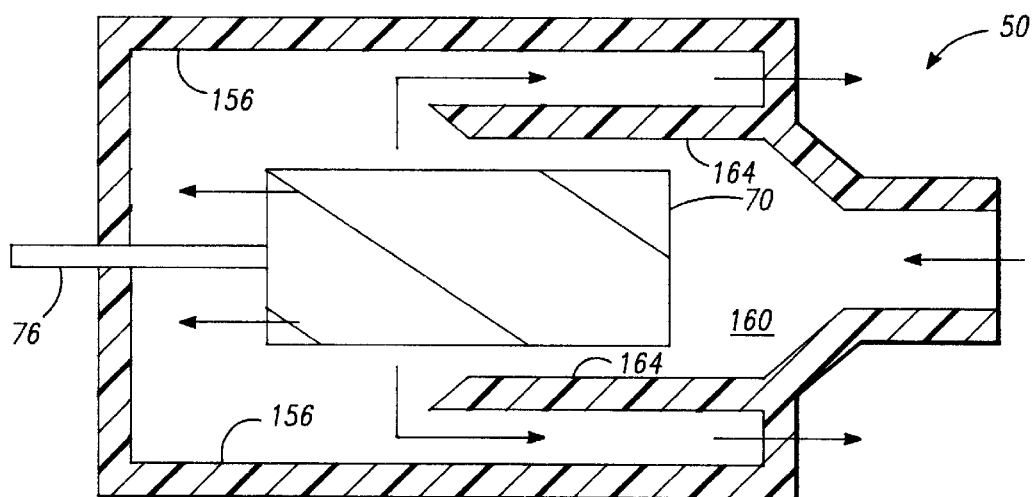

FIGS. 9A–E illustrate several simplified cross sections of various embodiments of the present invention. Each of the illustrated reverse flow pumps essentially consist of an outer pump housing and a rotor. The pump further consists of an inlet passageway and a separate outlet passageway to direct the flow of fluid as indicated by the arrows included in the figures for purposes of illustration. However, the direction of fluid flow may be reversed by changing the direction of the rotor movement or by varying the rotor blade configuration. In FIGS. 9A and 9B, an additional interior compartment 160 is included within the outer pump housing 152. The interior compartment 160 may be formed with walls 162 or 164 that surround at least a portion of the rotor 70. The interior compartment 160 may alternately be described as an inlet tube when fluid is drawn into the pump 50 within this region before being expelled through the region defined by the outer pump housing 152 and the interior compartment. Although the inlet compartment 160 and the pump housing 152 shown throughout FIGS. 9A–E in section are preferably cylindrical, they may of course be altered accordingly for different applications.

The reverse flow pump shown in FIG. 9A may be described as an axial flow pump in view of the generally axial direction of the fluid flow relative to the shaft 76 of the rotor. In this particular embodiment of the present invention, the walls 162 of the interior compartment 160 extend circumferentially around the rotor 70 to direct the fluid in an axial direction towards the base 154 of the pump housing 152 before being directed away from the pump 50 in the region defined by the interior compartment 160 and the outer pump housing 152. In FIG. 9B, the reverse flow pump shown may be described as a centrifugal flow pump in accordance with the general outwardly direction of the fluid flow relative to the shaft 76 of the rotor 70. In this particular embodiment of the present invention, the walls 164 of the interior compartment 160 extend around a portion of the rotor 70 to direct the fluid in a general direction towards the housing walls 156 of the pump housing 152 before being directed away from the pump 50 in the region defined by the interior compartment 160 and the outer pump housing 152.

Figure 9C:
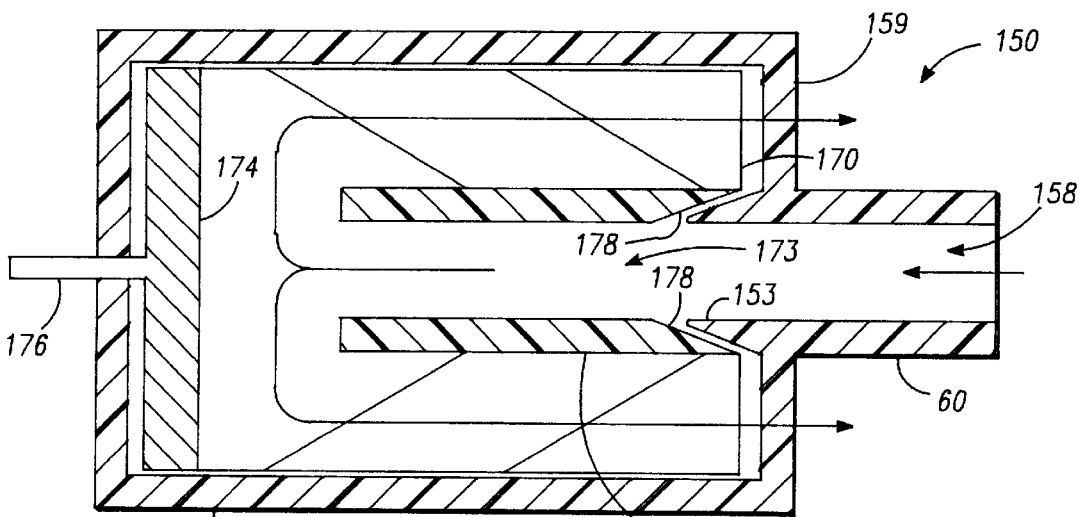
Figure 9D:
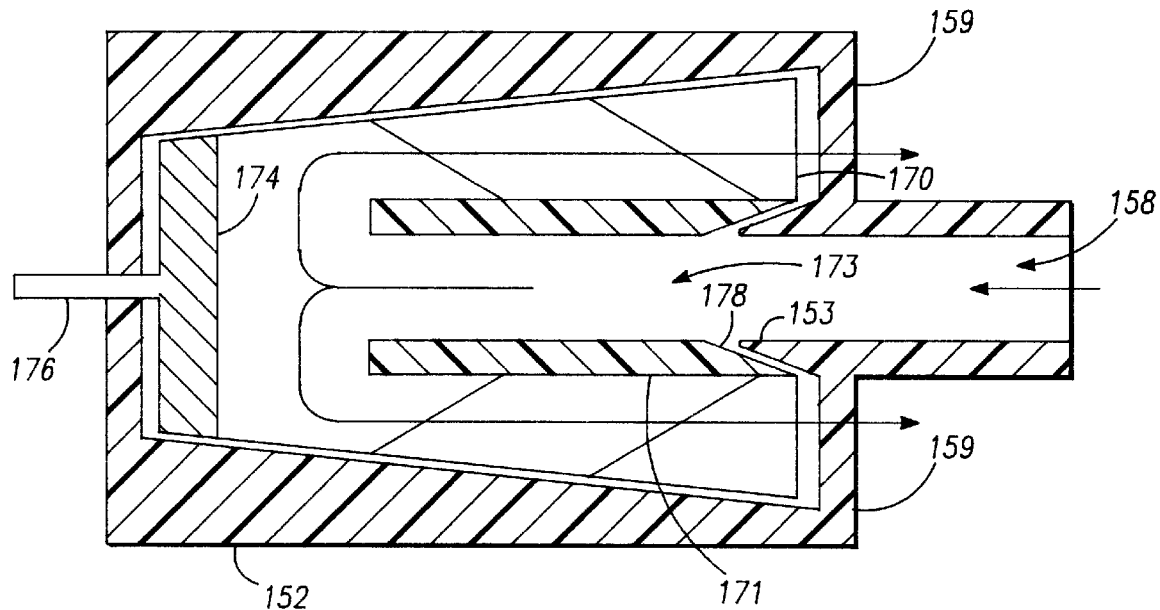

FIG. 9C illustrates another variation of the present invention that includes a reverse flow pump 150 with a hubless rotor 170. The hubless rotor 170 basically consists of a central portion 171 that is positioned within the pump housing 152 by supporting members and a rotor base plate 174. The rotor 170 may also be formed with a tapered opening 178 corresponding to a tapered opening 153 formed in the housing cap 60 to form a relatively close fit. The hubless rotor 170 of the reverse flow pump tends to draw fluid entering the pump away from the unit so as to reduce the direct impact of the fluid against housing walls or the base of the pump. In this manner, a reverse flow pump with a hubless rotor may be characterized as both an axial and a centrifugal flow pump that embodies characteristics of each configuration. A relative degree of improved efficiency has been observed with the hubless rotor configuration shown in FIG. 9C as compared to the rotor designs illustrated in FIGS. 9A and 9B. Satisfactory flow rates are achieved nonetheless with these and other rotor configurations for the present reverse flow pump.

Figure 9E:
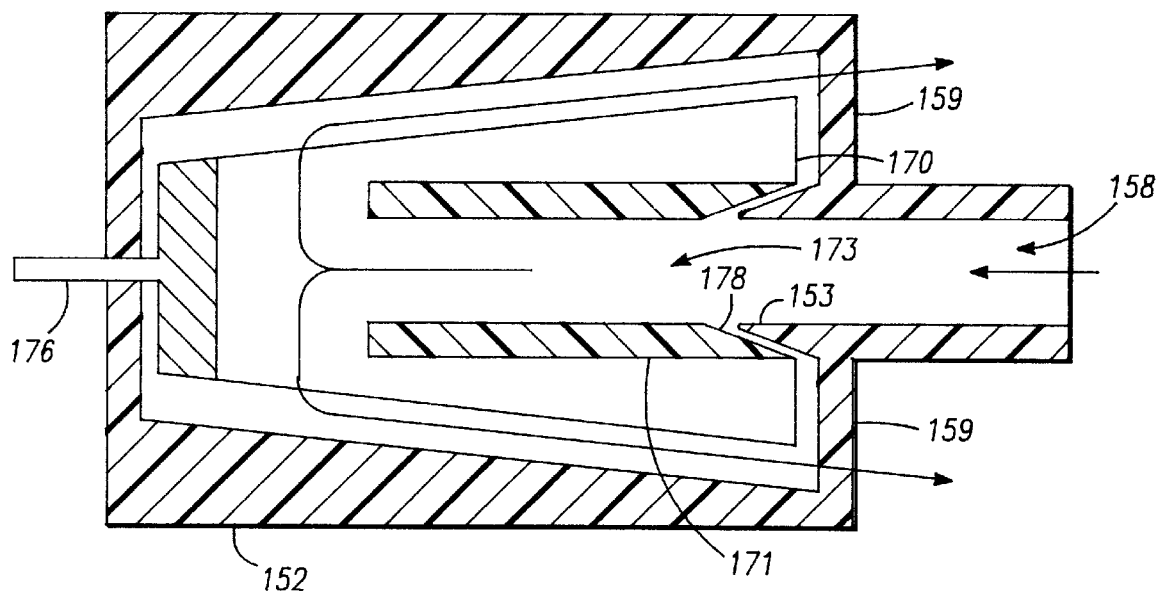

The various rotor designs that may be used in accordance with the principles of the present invention include rotors having central passageways with externally formed blades, internally formed blades, or with no blade portion at all. For example, in FIG. 9D, a hubless rotor is shown with external blades in partial conical form. The periphery of the rotor 170 in this variation generally conforms to the inner surfaces of the pump housing 152 while still permitting the passage of fluid around the outer surface of the rotor. At the same time, a hubless rotor 170 may also have blades formed internally within the central portion 171 (not shown), or with no rotor blades as shown in FIG. 9E which may be referred to as a shear pump design. The reverse flow pump 150 and rotor assemblies shown in FIGS. 9C–E generally permit fluid to travel through the center of the rotor 170 ordinarily occupied by a central hub. The open passageway 173 formed in the central portion 171 of the hubless rotor 170 permits fluid to be drawn into the reverse flow pump 150 and subsequently directed away from the pump. As indicated by the directional arrows drawn in FIGS. 9C–E, the open passageway 173 may be aligned with the inlet passageway 158 of the pump housing 152, and the region external of the central portion 171 of the hubless rotor 170 may be aligned with the outlet passageway 159 of the pump 150.

Figure 10:
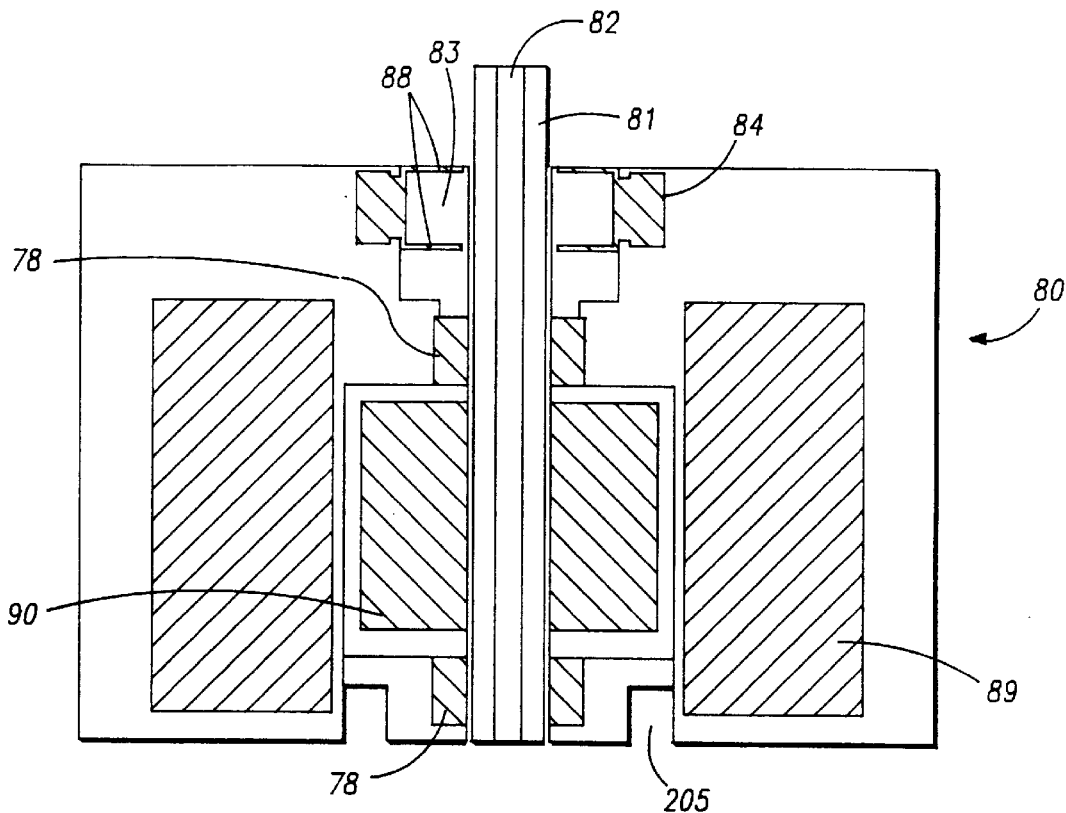
FIG. 10 is a simplified sectional side view of the drive unit for a reverse flow pump assembly.

FIG. 10 illustrates a drive unit 80 that may be used in accordance with the present fluid control and delivery system. The drive unit 80 may be a miniature electric motor with an outside diameter equal to or less than the outside diameter of a housing body. The drive unit 80 may also be a pneumatic driven turbine that is used to transform energy from a pressurized source to a rotary motion of shaft 81 or any other device that could impart rotation. The proximal face of the drive unit 80 may comprise a groove 205 for attachment to the distal end of a positioning rod 273 (shown in FIGS. 3 and 4). A central passage 82 with a diameter of approximately 0.040 inches may also extend through the entire length of the shaft 81. The shaft 81 may be coupled directly or indirectly to a rotor and transmit any shaft rotation to rotor rotation. A blood seal 84 may be attached to the drive unit 80 and may comprise a central cavity 83 containing a biocompatible lubricating fluid, such as nutrilipid, dextrose solution, glycerin, or alike. The blood seal 84 may further comprise two thin lips 88 that engage the outside diameter of shaft 81 to form a closed chamber to retain the lubricating fluid inside the central cavity 83 during the pump operation. Alternate blood seal designs well known in the art may also be used in the drive unit 80. A 40% dextrose solution may also be used as a lubricating fluid with a continuous infusion of dextrose into the seal area. When the selected drive unit is electrical, as shown in FIG. 10, an electric stator 89, a magnetic rotor 90 and two bearings 78, may be used in a conventional method to transform electric energy into rotational motion. Furthermore, when the pump or fluid transport apparatus is positioned without the use of a guide element, such as guide wire, catheters and like devices, the central passage 82 formed in the shaft 81 of the drive unit 80 may be removed or used for functions other than a passage for a guiding element.

Figure 11:
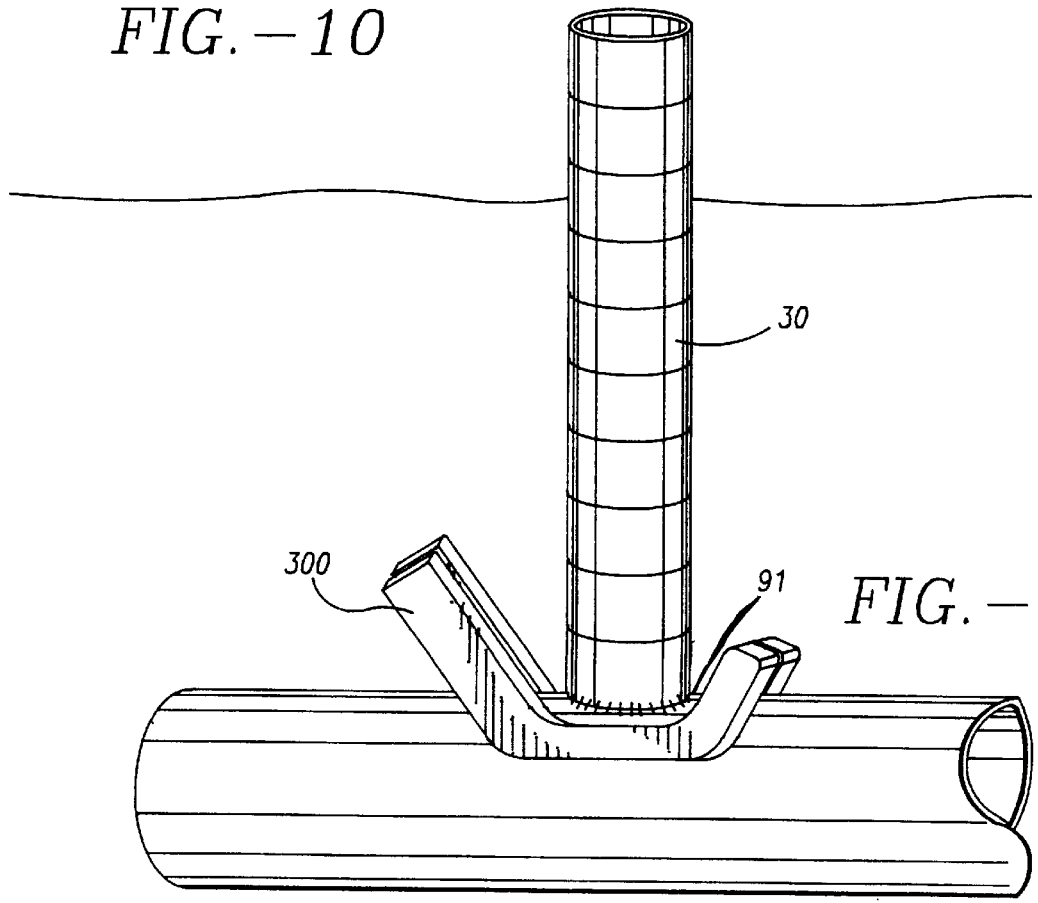
FIG. 11 is a simplified perspective view of a conduit formed by conventional techniques showing a clamped vessel and an attached conduit.

As shown in FIG. 11, the installment of fluid transport apparatus often includes the anastomosis of the distal end of the outer conduit 30 to the sides of a targeted blood vessel or chamber using thoracoscopic suturing, or microstapling. Prior to suturing the outer conduit 30 to a blood vessel or cavity wall, the vessel or wall portion may be isolated by using a C-clamp, thoracoscopic clamps, or any other type of similar clamp 300 that is capable of assisting in forming small ports into the body of a patient, and preferably capable of isolating only a section of the wall without complete occlusion of the vessel.

Figure 12:
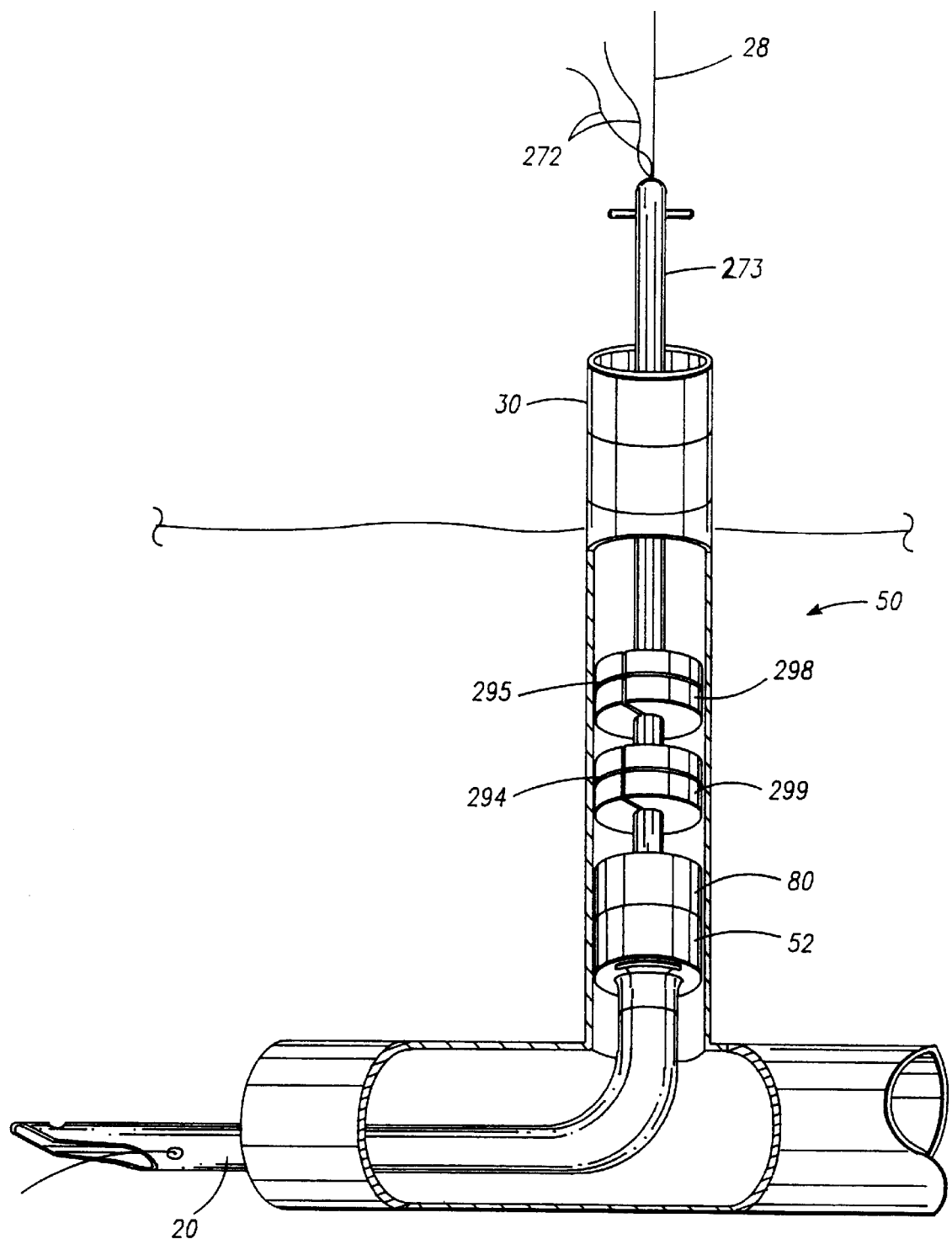
FIG. 12 is a simplified sectional perspective view of a reverse flow pump assembly positioned within the conduit shown in FIG. 11.
Figure 13:
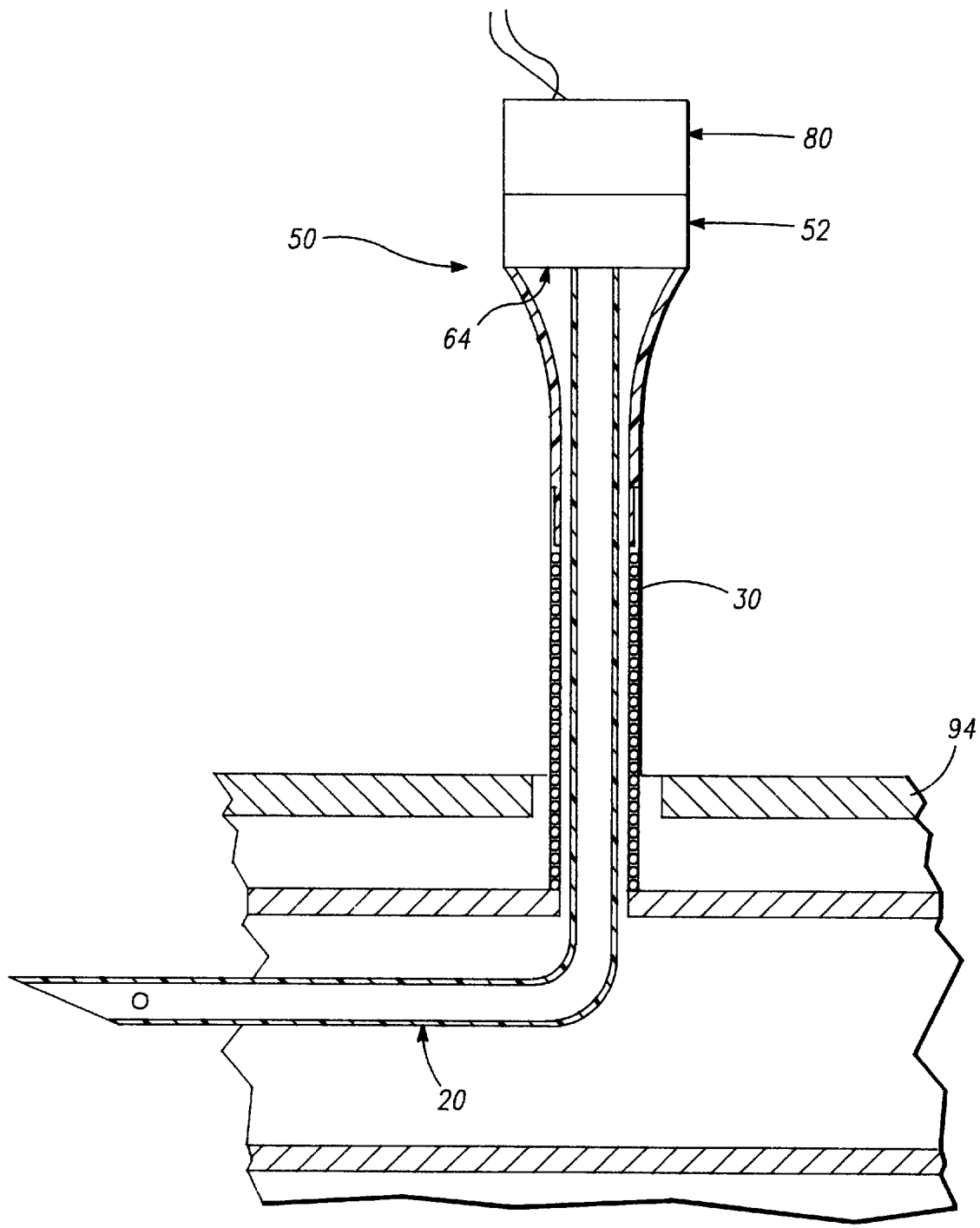
FIG. 13 is a simplified sectional side view of a reverse flow system where the pump assembly is positioned external to a blood vessel graft.

After a portal 91 is created in the desired blood vessel or body cavity, as shown in FIGS. 11 and 12, the outer conduit 30 is inserted into the portal. A suture may be used to secure the outer conduit 30 in place relative to the portal 91. A commercially available high stiffness guide wire 28 may also be passed through the outer conduit 30 to assist in the placement of the inner cannula 20. The outer conduit or graft 30 may also be of sufficient length to accommodate the pump 50 from the distal end of cannula 20 to the proximal end of the positioning rod 273. Alternatively, the pump may be positioned externally relative to the outer conduit (as shown in FIG. 13). After placing the pump 50 in the outer conduit 30, the outer conduit may be filled with saline solution, and the pump may also be primed, if desired, to substantially remove the presence of air from the pump and the outer conduit. The driving unit 80 may then be installed in a proximal position relative to the pump 50. A proximal silicone plug 298 may be mounted on the positioning rod 273 and advanced to seal the outer conduit 30 and the driving unit 80. A suture may be tied on the outside of the outer conduit 30, and in the area of the graft overlaying proximal groove 295 of the proximal silicone plug 298 to secure the plug to the proximal part of the conduit. After the installation of the fluid transport apparatus 10, the C-clamp is released gradually, and homeostasis at potential bleeding sites are visually examined unassisted or with the aid of a viewing scope. Upon achieving acceptable homeostasis or stability, the C-clamp 300 may be completely released but should be kept in ready position to clamp the anastomosis site in case of an emergency. A guide wire 28 may be also advanced with the help of imaging techniques to dispose the distal end of the inner cannula 20 in the desired blood vessel, heart chamber or other body cavity. The guide wire 28 may be inserted and positioned to a desired location before being passed through an opening or orifice formed on the distal end of the inner cannula 20. As a result, the distal end of the inner cannula 20 may be guided to a location before removing the guide wire 28. While positioning the distal end of the inner cannula 20, the pump 50 may need to be advanced in the outlet conduit 30 by pushing the positioning rod 273 into the outer conduit or graft. When pump 50 reaches the desired position, the distal silicone plug 299 may be advanced to the proximal side of the drive unit 80 and secured in place by a suture, a laproscopic clamping device, or other similar techniques. A suture or a laproscopic clamping device may be employed to hold the apparatus in position or the outside diameter of the housing body 52 may also be secured to the outer conduit or graft 30 using similar techniques to secure the distal plug 299. After securing the pump 50 to the graft, the guide wire 28 may be removed before the pump is activated. Alternatively, the guide wire 28 may be removed immediately after positioning the inner cannula 20 relative to the outer conduit 30. The pump 50 may then be secured to the proximal ends of the inner cannula 20 and the outer conduit 30. Accommodations for passage of the guide wire 28 through other components of the fluid transport apparatus may thus be avoided.

After the pump 50 is activated, medication or drugs for slowing or completely stopping the heart may be administered when used to support cardiac functions. The pumping rate of the pump 50 may be adjusted to maintain sufficient circulation or to accommodate changes in circulatory demand. The pump 50 may also be equipped with sensing devices (not shown) for measuring various body conditions such as the blood pressure, the presence of blood, or other parameters that would suggest the need for altering the flow rate of the fluid transport apparatus 10. For example, the apparatus may include pressure sensors along the inner cannula 20 so that a preset pressure change would signal the need to change the pumping capacity of apparatus. The pump 50 may include sensors to sense the pressure at the distal end of the cannula 20 so that a preset pressure change could signal the need to change the pumping capacity of pump. When the pressure at the distal end of inner cannula 20 decreases by a certain increment, which indicates the commencement of pump suction, a controller used with the apparatus 10 may provide warning signals or automatically decrease the flow rate of the apparatus until returning to a preset pressure at the inner cannula.

In the removal of the fluid transport apparatus, the suture or laproscopic clamping device for the apparatus is first disconnected enabling it to be moved. The silicone plugs 298 and 299 and housing body 52 are freed and removed. The pump 50 is then retracted through the outer conduit 30, and the C-clamp 300 is engaged and clamped to isolate the portal site. The anastomosis may be restored using common thoracoscopic techniques for suturing or stapling before being removed. Finally, the surgical site is closed using known surgical techniques.

When the present fluid support apparatus is selected for circulatory support of the heart, a method for effectively transporting blood between regions of the heart may basically include: selecting a blood flow support apparatus 10 including a coaxially aligned inner cannula 20 and an outer conduit 30, a coaxially aligned reverse flow pump 50 disposed therebetween; forming a portal 91 in a blood vessel in communication with the heart; connecting the outer conduit through the portal; inserting the inner cannula through the outer conduit and the portal so that the distal opening 22 of the inner cannula is disposed on opposite sides of a desired heart valve or region relative to the distal opening 32 of the outer conduit, and activating the reverse flow pump so that blood adjacent to the distal opening of the inner cannula is pumped through the inner cannula to the outer conduit.

As shown in FIG. 12, a guide wire 28 may be advanced with the help of imaging techniques to any of the heart chambers or vessels. In preparation for insertion of a fluid transport system into a patient, a commercially available high stiffness guide wire 28 may be used and passed through the central passage of the positioning rod 273 proximal end, to the distal end of the rotor 70, passing through the gland valve 77, and through the cannula 20. The pump 50 and the guide wire 28 may be are inserted into a graft or outer conduit 30 and advanced to the clamped section of a vessel.

In another embodiment of the present invention shown in FIG. 13, the pump 50 may be sealed and attached to the outer conduit 30 with an external drive unit 80. This variation includes the use of a pump 50 that is kept outside the skin of a patient 94 wherein the pump attaches to the proximal end of graft 30. The outer conduit or graft 30 is anastomosed as described above, but the pump 50 is not inserted into the inside diameter of this outer conduit. Rather, only the distal end of the main outflow housing 52 is inserted into the outer conduit 30 and secured by using a suture tied around the outside diameter in the area overlapping the outer conduit. The pump 50 outflow discharges from outflow windows 64 into the inside diameter of outflow housing 52. An advantage offered by this embodiment of the present invention is the use of a pump 50 that is kept outside the skin 94. This variation effectively avoids the requirement for both the pump housing body 52 outside diameter and the outside diameter of the drive unit 80 to be smaller than the inside diameter of the outer conduit 30. The outside diameter of the pump rotor and all internal parts dimensions may therefore be larger than described earlier, which may simplify the pump designs, and may enable the device capacity to be increased significantly without increase in pump design sophistication. As with other embodiments of the present invention, this variation may obviously be used with patients that already have their body open for a surgical procedure wherein graft 30 is not passed through the skin to access a vessel, heart, cavity, or any other body region.

Figure 14:
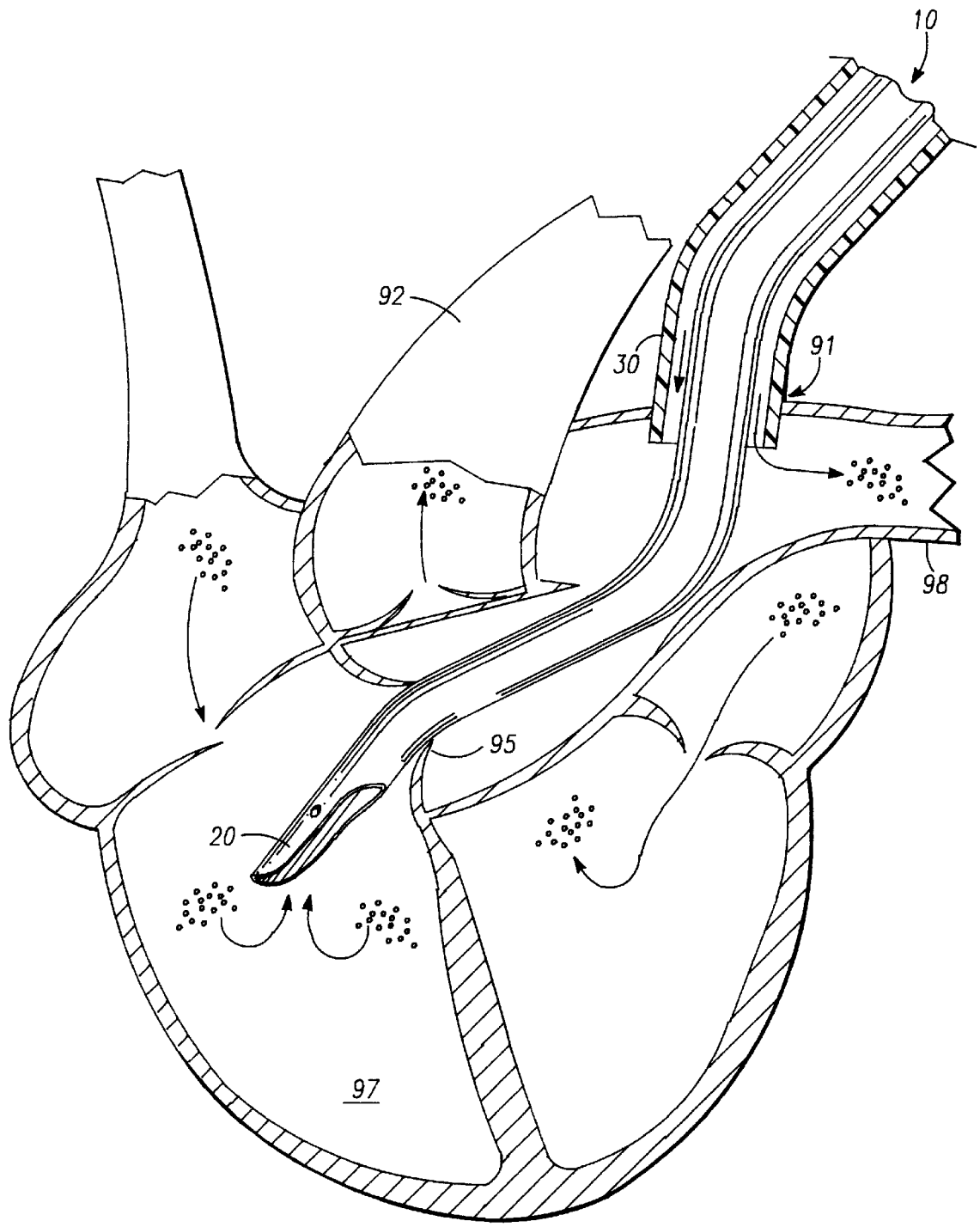
FIG. 14 is a sectional view of a heart and its respective chambers and valves including the placement of an inner cannula and an outer conduit for assisting the transport of blood between different regions of the heart.

FIG. 14 is an illustration of another cardiac support apparatus 10 that may be used in accordance with the concepts of the present invention. The illustrated fluid transport apparatus 10 provides cardiac support to the right side of the heart by pumping blood from the right ventricle 97 to the pulmonary artery 98. In this instance, a portal 91 is formed in the pulmonary artery 98 through which the distal end of the outer conduit 30 is extended. The inner cannula 20 may be inserted into the portal 91 and through the pulmonic valve 95 to reach the right ventricle 97. Both the inner cannula 20 and the outer conduit 30 may of course be connected to a reverse flow pump, and may be further selected of appropriate lengths to facilitate endoscopic procedures or to provide on-site cardiac support which minimizes exposure of circulated blood with foreign surfaces.

Figure 15:
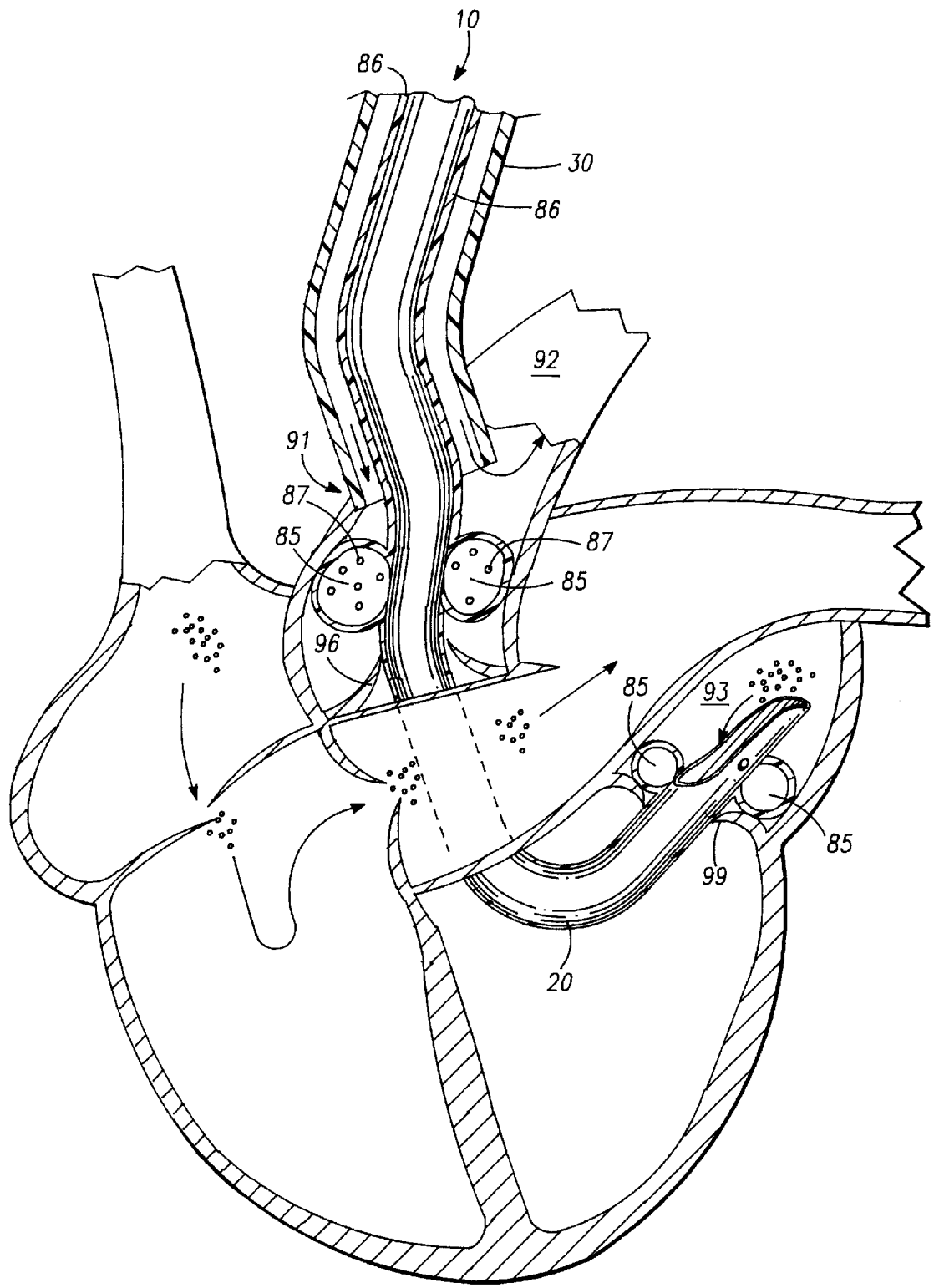
FIG. 15 is sectional view of the heart showing a portal formed in the aorta for the placement of the outer conduit and the inner cannula which also includes inflatable balloons positioned in different regions of the heart.

FIG. 15 is an illustration of another variation of a cardiac support apparatus 10 adapted particularly for left heart assistance. An outer conduit 30 is attached to a portal 91 formed in the aorta 92, and an inner cannula 20 is continuously extended through the portal 91, the aortic and mitral valves 96, 99, respectively, and eventually the left atrium 93. An optional balloon 85 may also be disposed on the outside surface of the inner cannula 20 to seal, or to deliver a cool fluid or mediation to the adjacent tissue. The balloon 85 may be disposed around the inner cannula 20 and connected to a conduit 86 through which air, or a suitable coolant, or mediation may be transported to the balloon 85. When the balloon 85 is used to deliver medication, a plurality of perforations 87 may be formed on the surface of the balloon 85 to allow medication to be delivered to the surrounding tissue. The inflatable balloon 85 may also create a separation in a body cavity to provide for the transport of fluid between the regions surrounding the distal end of the inner cannula 20 and the distal end of the outer conduit 30. In this configuration, the inner cannula 20 does not necessarily pass through body compartments separated by valves or other separating body members. For example, the inflatable balloon 85 may isolate an organ such as a kidney or seal a region of the body when pressurized within a body cavity or vessel. Fluid may be delivered under pressure from the inner cannula 20 to the region surrounding the outer conduit 30. Accordingly, the inflatable balloon 85 may be used alone or in conjunction with other variations of the present fluid transport and control system.

Figure 16:
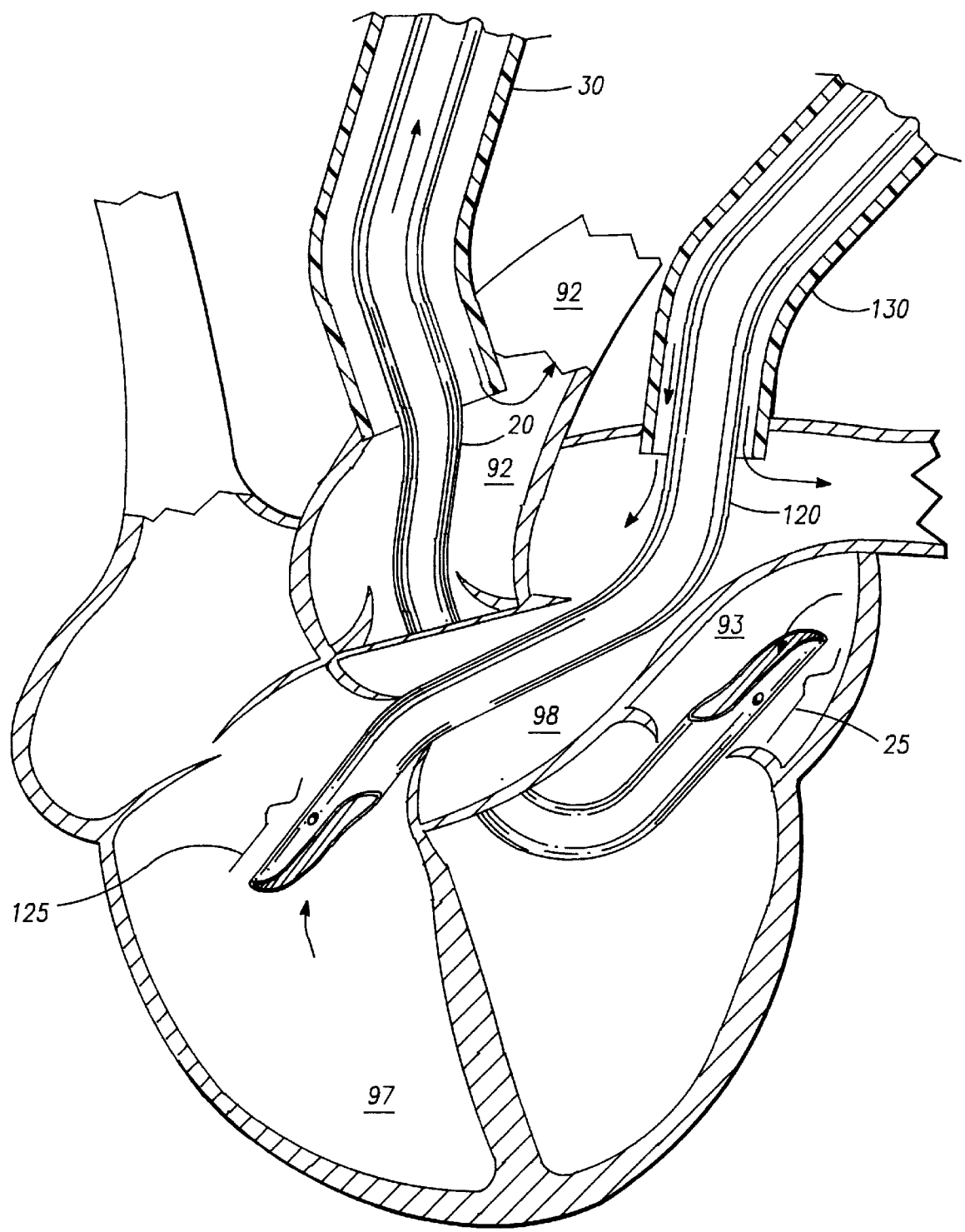
FIG. 16 is a sectional view showing the positioning of the inner cannulas and outer conduits of multiple circulatory support systems in different heart regions.

Another variation of the present invention is the insertion of a heart pump into the left heart side and simultaneously inserting a second heart pump into the right heart side of the patient as shown in FIG. 16. An inner cannula 20 may be placed in the left atrium and the second cannula 120 in the right ventricle. The inflow cannula tip 25 of cannula 20 placed in the left heart side may be advanced and placed in the left ventricle, left atrium, or any of the left heart vessels. Meanwhile, the inflow cannula tip 125 of the second cannula 120 may be placed in the right heart side and advanced into position in the right ventricle, right atrium, or any of the right heart vessels. Whether the heart pumps of the present invention operate in unison, or singularly, the circulatory functions of the heart may be supported in open or closed heart surgery without necessarily immobilizing or arresting the heart which would further require extensive surgical procedures and apparatus.

Figure 17:
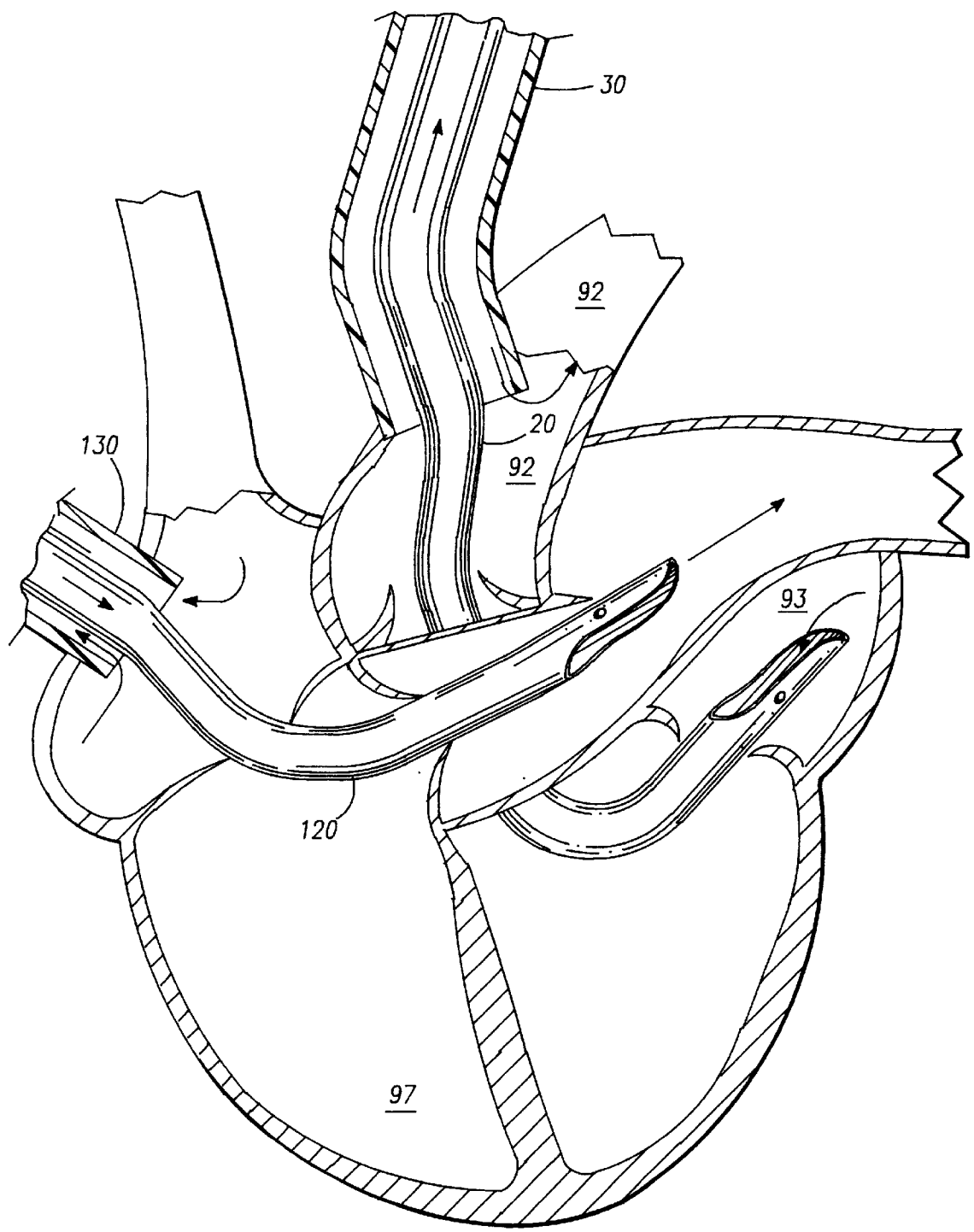
FIG. 17 is a sectional view showing a dual circulatory support system supporting both the left and right side of the heart.

FIG. 17 illustrates another variation of the present invention involving the insertion of a left heart pump into the left side of the heart, and simultaneously inserting a second heart pump into the right side of the heart. A cannula 20 may be placed in the left atrium and a second cannula 120 from another pump may be placed in the pulmonary artery and passed through the vena cava, right atrium, and right ventricle. The heart pumps shown are similar except that cannula 20 of the left heart pump may function as inflow cannula while cannula 120 of the second pump may function as an outflow cannula as earlier described. An outer conduit 30 when used with left heart pump may function as an outflow cannula while the outer conduit when used with the second pump may function as an inflow cannula. As discussed above, the second cannula 120 may have all of characteristics and capabilities of the first cannula 20.

Figure 18:
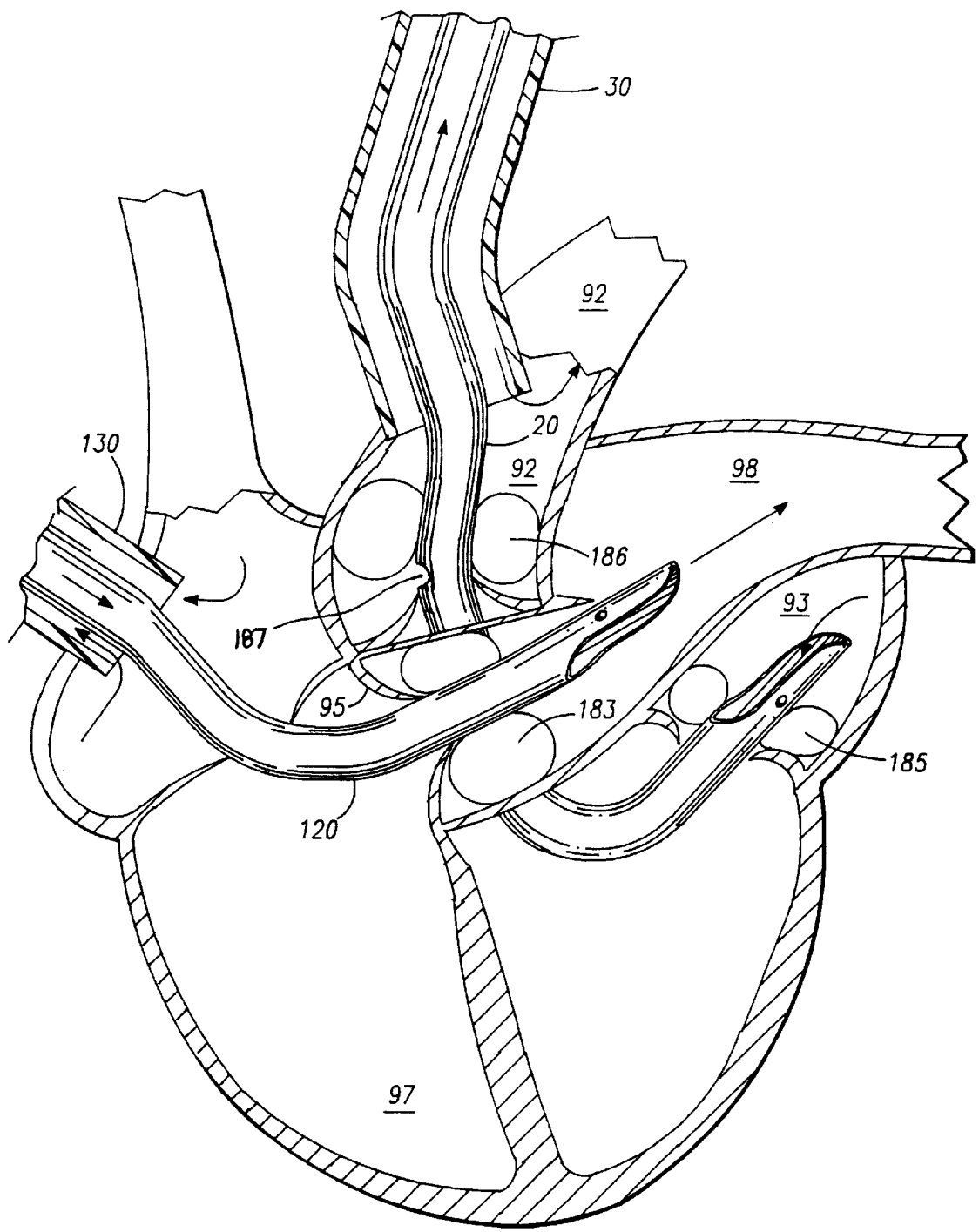
FIG. 18 is a sectional view of a dual circulatory support system further including inflatable balloons and ports formed along the inner cannula that are positioned in different regions of the heart.

Another variation of the present invention is the insertion of a left heart pump into the left heart side, and simultaneously inserting a second heart pump into the right heart side of the patient as shown in FIG. 18. The cannula 20 in this embodiment may comprise a distal balloon 185 for occluding the mitral valve, and a proximal balloon 186 for occluding the ascending aorta below the anastomosis site, and an orifice 187 for injection or suction of a fluid. Another cannula 120 from a second pump may also comprise a distal balloon 183 for occluding the pulmonic valve. However, as explained above, the second inner cannula 120 in this variation of the present invention serves as an outflow conduit while the outer conduit 130 serves as an inflow conduit. Another alternative provides for the occlusion of the mitral valve and the pulmonic valve of the patient, but not the occlusion of the ascending aorta. By operating both pumps, the heart may be partially or completely unloaded, and arrested by infusing drugs into the heart itself through the fluid orifice 187. As a result, this procedure provides a minimally invasive and less traumatic technique to maintain heart functions, and may be particularly suitable for endoscopic applications.

Figure 19:
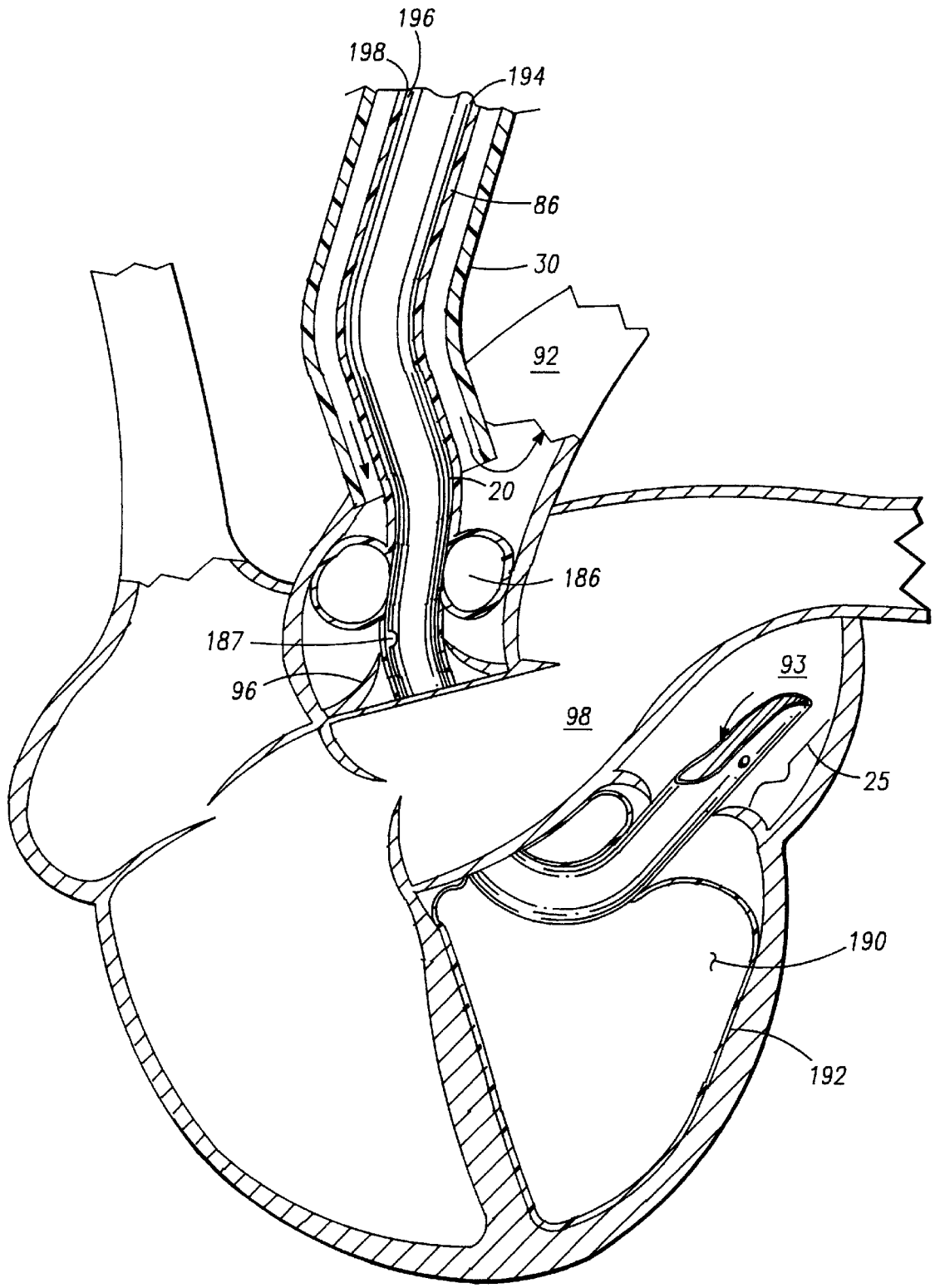
FIG. 19 is a sectional view of the heart illustrating a circulatory support and stabilization apparatus embodying multiple aspects of the present invention including at least one inflatable balloon in a heart region, a balloon within a heart chamber having another surrounding inflatable balloon, and further including additional openings formed along the inner cannula.

FIG. 19 illustrates another variation of the present invention which includes a cannula 20 extending through an outer conduit 30. The cannula 20 of the pump may also be formed with multiple balloons on the outside diameter of cannula 20 that may be inflated through separate or common ports located outside the patient's body with air or fluid. A balloon 186 that may be formed at any position along cannula 20 may be inflated through a port and passageway 194 located outside of the patient's body with air or fluid to force a heart cavity to stretch. The balloon 186 may also be inflated to occlude a vessel, a cavity, a heart chamber, or a wound in any tissue or organ, or it may be filled with air or fluid of a lower or higher temperature than the surrounding tissue to cool or to heat a vessel, a cavity, a heart chamber, or a wound in any tissue or organ. The balloon 186 may also be inflated to hold a heart valve open, to hold a flap open, or to hold any internal structure in a desired position. Another balloon 190 may also be inflated through a port and passageway 196 located outside the patient body with air or fluid and force this second balloon 190 against the wall of a vessel, a cavity, a heart chamber, or a wound in any tissue or organ. This balloon 190 may further include a surrounding balloon 192 that may be perforated and used to inject drugs, cardioplegia solutions to arrest the heart, or any other therapeutic agent through the balloon perforations to treat, affect or alter the tissue in contact with balloon. The surrounding balloon 192 may similarly be inflated through a common port with its adjoining balloon 190, or a separate port and passageway 198 located outside the patient body with a variety of drugs or therapeutic agents. The ports and passageways of all the aforementioned balloons may be formed adjoining to or concentric with the cannula 20. An orifice 187 may also be formed in the cannula 20 and located between two balloons to serve as an inflow port in conjunction with the cannula tip 25, or when the cannula tip may become occluded. The orifice 187 may also be positioned anywhere along cannula 20 surfaces. The orifice 187 may alternatively be used as an injection port, a port for measuring pressure in areas proximal to the orifice or a suction port that could be accessed from a port located outside of the patient's body. The orifice 187 and the inner lumen of cannula 20 may of course be separated, and may not affect each other and their respective functions.

Another aspect of the present invention includes stabilization apparatus and related methods for providing relatively stable surgical sites as shown in FIG. 20. The stabilization system 410 may basically comprise a stabilization cannula 411 with an inner passageway 414 for fluid transport that is formed of a reinforced wire 418 with a proximal end 413 and a distal end 415, an inflation lumen 412, and an inflatable stabilization balloon 440 attached to the outer surface of the cannula. The stabilization balloon 440 may also be shifted relative to the stabilization cannula to allow the stabilization of different areas of the heart, and may be formed of two different devices, and not integral formed as one device, that are designed to work together to achieve the described function above. The balloon 440 may be formed of permeable material that will allow diffusion of a fluid that may also be used to inflate the balloon towards the outside surface of the balloon. The fluid may also contain a number of drugs used to affect the area in direct contact with the balloon 440 or be used to control the temperature of tissue in the proximity of the balloon. The stabilization cannula 411 is preferably made from a thin wall elastomeric material, such as silicone or urethane, and may include encapsulated wire material 418 to provide some degree of kink resistance. The inflation lumen 412 may be a tubular section connecting an open proximal end 417 with a miniature side opening 416, and a blocked distal end 419. The distal end 419 may be blocked by adhesive or alike methods to contain any fluid in inflation lumen 412 from leaking out. The inflation lumen 412 may be in communication with the balloon interior 442 via a small side opening 416 in inflation lumen 412. The inflation lumen 412 may be in communication with the outside of the body through one of the catheter lumens 422. The injection of any fluid at the proximal end 417 or through catheter lumen 422 assists in the inflation of inflatable balloon 440.

The stabilization apparatus 410 and a pump 420 may be introduced into the body as shown in FIG. 21 through the femoral artery 430 with a catheter 428 linking the device to the exterior of the body. The catheter 428 may be a multi-lumen catheter with separate lumens to drive the pump 420, to measure pressure in the vicinity of the catheter along its entire length, to deliver or remove fluid, to enable the passage of small diameter guides or leads, or to perform other similar functions. Other lumens may be included in the catheter 428 to measure pressure, deliver or aspire fluid, for guide wire or tools passage, or usage of a catheter lumen. The stabilization cannula 411 further includes a distal end 415 and a stabilization balloon 440 with an interior 442. The distal end 419 of the inflation lumen 412 may be blocked and have an opening to inflate the balloon interior 442. The external surface of the heart 446 may be stabilized, as shown in FIG. 22, by using commercially available tools 447 (such as CTSI Stabilizer) that may be forked to hold a specific section of the heart from moving outwardly. Meanwhile, the stabilization cannula 411 may be positioned within a ventricle or atrium. After proper positioning, a pump may be activated and take over the left ventricle function. The balloon 440 may be inflated until the ventricle wall is restrained from inward movement. The heart wall therefore becomes relatively fixed and reduces any significant movement in order to allow the surgeon to perform delicate procedures such as suturing a still vessel. The balloon 440 may also be inflated so as to not entirely occlude the area it occupies in order to allow blood or other liquids to flow around the balloon. The stabilization cannula 411 and balloon 440 may also be positioned in an atrium instead of a ventricle to fixate the heart wall at the atrium level instead of the ventricle level. The right side of the heart may be accessed through the femoral vein, the neck or arm arteries, through direct insertion into the right atrium or right ventricle, through the pulmonary artery, or any vein of the adequate size. Alternatively, a mechanical structure may be employed instead of a balloon 440 to achieve the same stabilization described above. For example, any mechanical fixation may be used including hinged arms that have low profile during insertion, and may expand when advanced to the right position to provide support from the interior surfaces. Similarly, this stabilization apparatus 410 may further be used to hold the inside wall of an organ or a cavity such as the abdominal wall or hepatic conduits during surgery.

Figure 23:
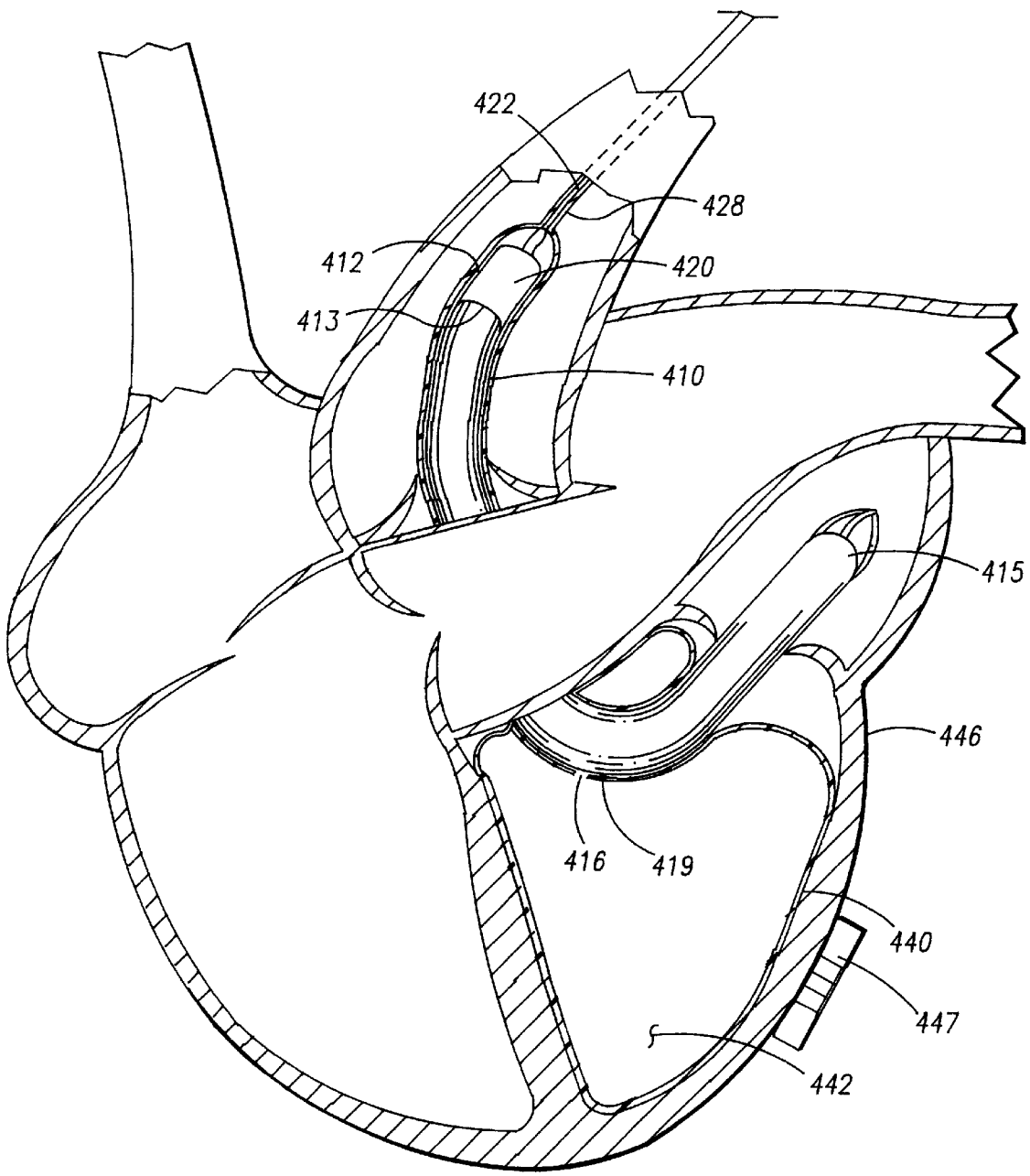
FIG. 23 is a partial sectional view of the heart and a stabilization system used in cooperation with an intravascular pump.

FIGS. 23 and 24 illustrate two different embodiments of the present invention. As shown in FIG. 23, the placement of stabilization apparatus 410 may be achieved by introducing the stabilization system alone, or with a pump 420, through the femoral artery 430 via direct aortic insertion, or through any other artery of adequate size, i.e., brachiocephalic, carotid, etc. The proximal end 413 or the distal end 415 of the stabilization system 410 may be adapted to receive a blood pump 420 to aid in moving fluid between both ends of the conduit. The blood pump is preferably mounted to the distal end 415 of the stabilization cannula 411.

FIG. 24 similarly illustrates positioning of another stabilization system formed in accordance with the present invention. An access conduit 433 such as a Dacron™ graft may be formed to receive an extracorporeal pump 421, or a reverse flow pump such as those described above, at the proximal end of the access conduit 433 and use the stabilization apparatus 410 for its inflow, and access conduit 433 for its outflow to result in a similar arrangement to the one described above and presented in FIG. 24. As explained above, the placement of the access conduit 433 may be achieved by common surgical methods used to graft a end-to-side graft. The stabilization systems shown in FIGS. 23 and 24 illustrate only some of the various types of commercially available intravascular and extracorporeal pumps that are compatible or provided for by the present invention.

While the present invention has been described with reference to the aforementioned applications, this description of the preferred embodiments and methods is not meant to be construed in a limiting sense. It shall be understood that all aspects of the present invention are not limited to the specific depictions, configurations or relative proportions set forth herein which depend upon a variety of conditions and variables including the types of bodily fluids that are transported, or controlled, the relative areas in which fluid is transported, the areas of the body which are being stabilized during surgery, and the use of any combination of the embodiments of the present invention. Various modifications in form and detail of the various embodiments of the disclosed invention, as well as other variations of the present invention, will be apparent to a person skilled in the art upon reference to the present disclosure. It is therefore contemplated that the appended claims shall cover any such modifications or variations of the described embodiments as falling within the true spirit and scope of the present invention.

What is claimed is:

1. A pump and coaxial lumen system for transporting bodily fluids, comprising:
   a pump housing having generally concentric inner and outer passageways;
   a rotor rotatedly disposed within said pump housing in fluid communication and generally axially aligned with the inner passageway for causing a generally reverse fluid flow between said inner and outer passageways; and
   first and second generally concentric conduits each having a lumen extending between a proximal end and a distal end, said proximal ends communicatively coupled to said inner and outer passageways, respectively, and said distal ends being separated by a distance.

2. The system as recited in claim 1 wherein said first conduit is an inner cannula and said second conduit is an outer cannula, and wherein said distal end of said outer cannula is adapted to be positioned within a portal formed within a living body.

3. The system as recited in claim 2 wherein the rotor is driven by a driving unit.

4. The system as recited in claim 3 further including an extension body having a lumen in communication with the pump housing and configured to be positioned within a percutaneous opening in the living body.

5. The system as recited in claim 4 wherein the driving unit is positioned within the extension body and arranged such that during use, the driving unit is external to the living body.

6. The system as recited in claim 5 wherein the system further includes a positioning rod and at least one silicon plug for placement of the driving unit within the extension body.

7. The system as recited in claim 1 further comprising at least one inflatable balloon disposed adjacent the inner cannula.

8. The system as recited in claim 7 wherein the balloon is in communication with a transport conduit formed along the inner cannula for inflating the stabilization balloon.

9. The system as recited in claim 7 wherein the inflatable balloon is formed with perforations to permit transmission of fluid through the balloon membrane to the external area surrounding the perforations of the balloon.

10. The system as recited in claim 9 further including a second inflatable balloon formed spaced apart and more proximate relative to the first inflatable balloon.

11. The system as recited in claim 2 wherein the system further includes at least one inflatable occluding balloon adjoining the inner cannula.

12. The system as recited in claim 2 wherein the inner cannula is formed with an orifice.

13. The system as recited in claim 12 wherein the orifice is in communication with an external pressure source.

* * * * *